(12) United States Patent
Hagaman et al.

(10) Patent No.: US 8,474,120 B2
(45) Date of Patent: Jul. 2, 2013

(54) BIFURCATED HIGHLY CONFORMABLE MEDICAL DEVICE BRANCH ACCESS

(75) Inventors: Logan R. Hagaman, Flagstaff, AZ (US); Cody L. Hartman, Flagstaff, AZ (US); Russell L. Jacoby, Flagstaff, AZ (US); Roark N. Wolfe, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 134 days.

(21) Appl. No.: 12/818,551

(22) Filed: Jun. 18, 2010

(65) Prior Publication Data

US 2011/0087319 A1 Apr. 14, 2011

Related U.S. Application Data

(60) Provisional application No. 61/250,313, filed on Oct. 9, 2009.

(51) Int. Cl.
*B23P 25/00* (2006.01)
*A61F 2/82* (2006.01)

(52) U.S. Cl.
USPC .......................................... 29/458; 623/1.35

(58) Field of Classification Search
USPC ........... 29/458, 469, 428, 505, 506; 623/1.13, 623/1.14, 1.15, 1.16, 1.18, 1.21, 1.22, 1.35; 156/252
See application file for complete search history.

(56) References Cited

U.S. PATENT DOCUMENTS

| 6,042,605 | A | 3/2000 | Martin et al. |
|---|---|---|---|
| 6,077,296 | A | 6/2000 | Shokoohi et al. |
| 6,352,561 | B1 | 3/2002 | Leopold et al. |
| 6,364,904 | B1 | 4/2002 | Smith |
| 6,645,152 | B1 | 11/2003 | Jung et al. |
| 6,645,242 | B1 | 11/2003 | Quinn |
| 6,737,158 | B1 | 5/2004 | Thompson |
| 7,306,729 | B2 | 12/2007 | Bacino et al. |
| 7,341,598 | B2 | 3/2008 | Davidson et al. |
| 7,413,573 | B2 | 8/2008 | Hartley et al. |
| 7,578,841 | B2 | 8/2009 | Yadin et al. |
| 2002/0103527 | A1 | 8/2002 | Kocur et al. |
| 2003/0199967 | A1 | 10/2003 | Hartley et al. |
| 2004/0230287 | A1 | 11/2004 | Hartley et al. |
| 2005/0059923 | A1 | 3/2005 | Gamboa |
| 2006/0229707 | A1 | 10/2006 | Khoury |
| 2007/0219621 | A1 | 9/2007 | Hartley et al. |
| 2008/0109066 | A1 | 5/2008 | Quinn |
| 2008/0114446 | A1 | 5/2008 | Hartley et al. |

(Continued)

FOREIGN PATENT DOCUMENTS

| WO | 97/21403 | 6/1997 |
|---|---|---|
| WO | 01/01886 | 11/2001 |

*Primary Examiner* — John C Hong
(74) *Attorney, Agent, or Firm* — Gilbert R. Gabo; Edward I. Amaya

(57) ABSTRACT

A method of making a multi-lumen stent graft includes covering a first mandrel that comprises a groove and a back wall of the groove with an innermost polymeric tube; slitting the innermost polymeric tube along the back wall of the groove; placing a second mandrel into the groove of the first mandrel and aligning the second mandrel with the back wall of the groove, deforming the innermost polymeric tube; placing an outermost polymeric tube over the innermost polymeric tube; and cutting an opening in the outermost polymeric tube over the second smaller mandrel, wherein the outermost polymeric tube and innermost polymeric tube comprise a graft member.

10 Claims, 18 Drawing Sheets

U.S. PATENT DOCUMENTS

2008/0269866 A1 10/2008 Hamer et al.
2008/0269867 A1 10/2008 Johnson
2009/0043376 A1 2/2009 Hamer et al.
2009/0048663 A1 2/2009 Greenberg
2011/0087318 A1* 4/2011 Daugherty et al. .......... 623/1.13

* cited by examiner

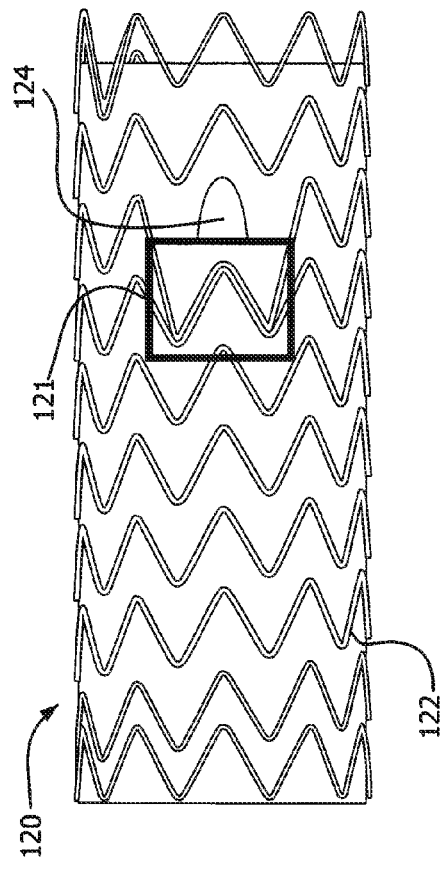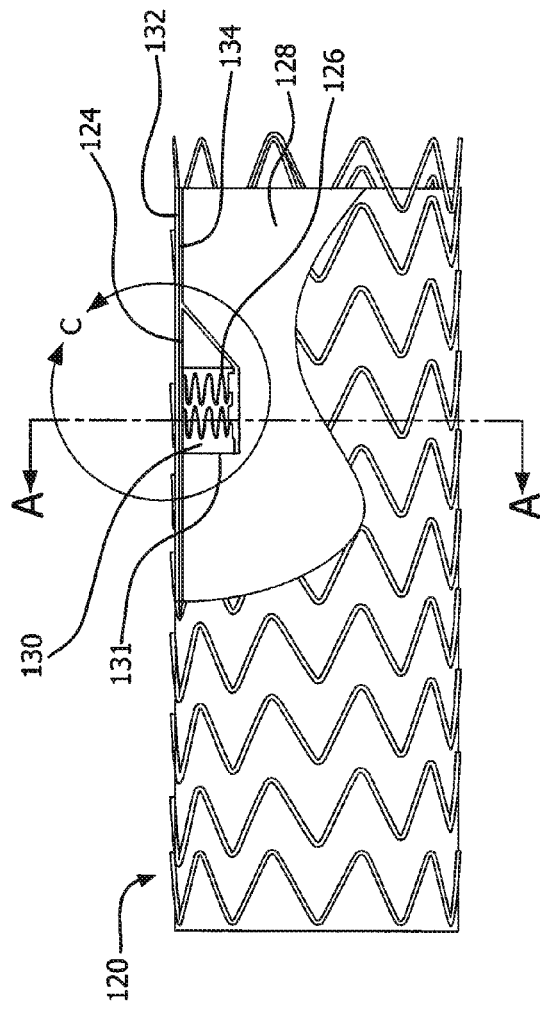
FIG. 1B
FIG. 1C

SECTION A-A

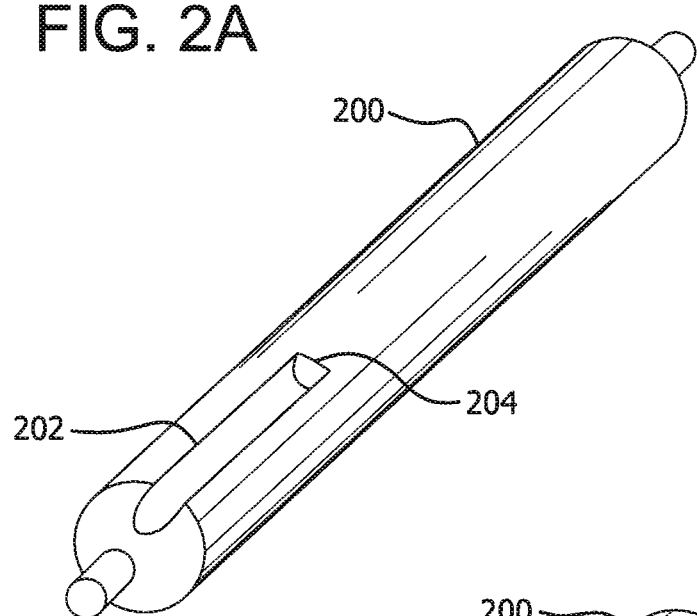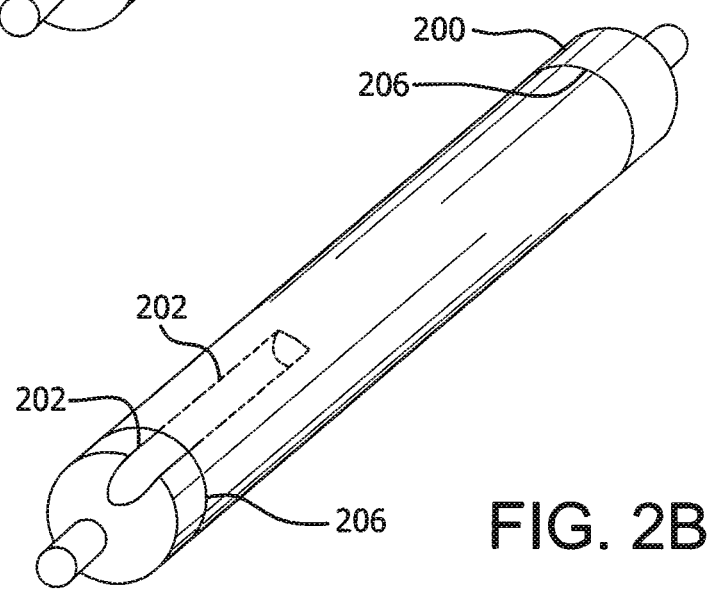

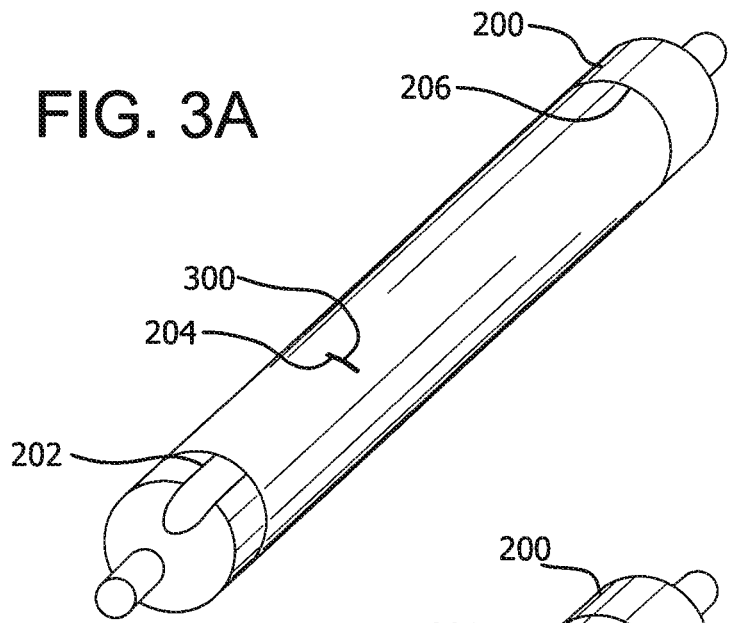
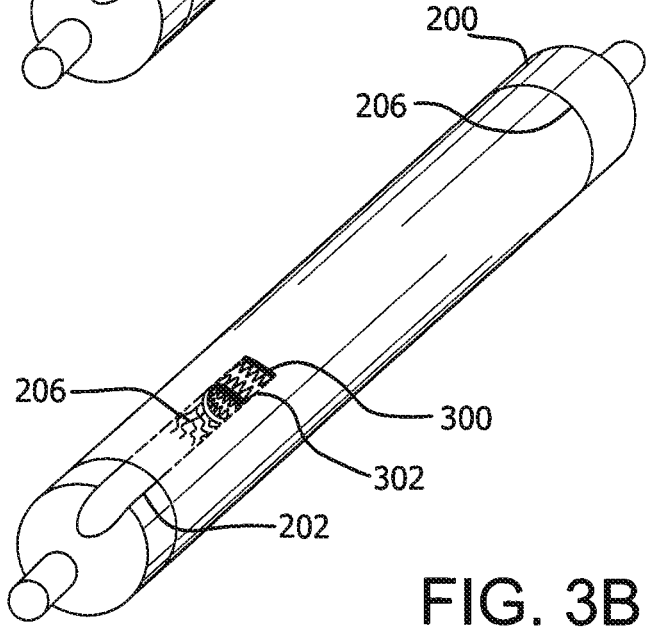

BIFURCATED HIGHLY CONFORMABLE MEDICAL DEVICE BRANCH ACCESS

CROSS-REFERENCE TO RELATED APPLICATIONS

This application claims benefit to U.S. Provisional Patent Application Ser. No. 61/250,313 filed Oct. 9, 2009, which is incorporated by reference herein for all purposes

FIELD OF THE INVENTION

One aspect of the invention is directed to an improved, modular, bifurcated stent graft having an integral support tube. Another aspect of the invention is directed to a highly conformable stent graft with an optional bifurcation.

BACKGROUND

Aneurysms occur in blood vessels at sites where, due to age, disease or genetic predisposition of the patient, the strength or resilience of the vessel wall is insufficient to prevent ballooning or stretching of the wall as blood passes through. If the aneurysm is left untreated, the blood vessel wall may expand and rupture, often resulting in death.

To prevent rupturing of an aneurysm, a stent graft may be introduced into a blood vessel percutaneously and deployed to span the aneurysmal sac. Stent grafts include a graft fabric secured to a cylindrical scaffolding or framework of one or more stents. The stent(s) provide rigidity and structure to hold the graft open in a tubular configuration as well as the outward radial force needed to create a seal between the graft and a healthy portion of the vessel wall and provide migration resistance. Blood flowing through the vessel can be channeled through the luminal surface of the stent graft to reduce, if not eliminate, the stress on the vessel wall at the location of the aneurysmal sac. Stent grafts may reduce the risk of rupture of the blood vessel wall at the aneurysmal site and allow blood to flow through the vessel without interruption.

However, various endovascular repair procedures such as the exclusion of an aneurysm require a stent graft to be implanted adjacent to a vascular bifurcation. Often the aneurysm extends into the bifurcation requiring the stent graft to be placed into the bifurcation. A bifurcated stent graft is therefore required in these cases. Modular stent grafts, having a separate main body and branch component are often preferred in these procedures due to the ease and accuracy of deployment. See U.S. Patent Application No. 2008/0114446 to Hartley et al. for an example of a modular stent graft having separate main body and branch stent components. In the Hartley et al. publication the main body stent has a fenestration in the side wall that is tailored to engage and secure the side branch stent. The side branch stent in such a configuration is in a "line to line" interference fit with the main body fenestration, causing a potential compromise to the fatigue resistance of the stent to stent junction. U.S. Pat. No. 6,645, 242 to Quinn presents a more robust stent to stent joining configuration. In the Quinn patent, a tubular support, internal to the main body stent, is incorporated to enhance the reliability of the stent to stent joining. The tubular, internal support of Quinn provides an extended sealing length along with improved fatigue resistance. However, the innermost tube is made by adding additional material shaped into a tube and sewn and/or adhered to the main graft component.

In addition, Aneurysms occurring in the aorta, the largest artery in the human body, may occur in the chest (thoracic aortic aneurysm) or in the abdomen (abdominal aortic aneurysm). Due to the curvature of the aortic arch, thoracic aortic aneurysms can be particularly challenging to treat. Other parts of the vasculature, such as the common iliac artery which extends from the aorta, can also be extremely tortuous. Hence, a stent graft deployed into such regions is preferably able to conform to the vasculature. The high degree of conformability allows the stent graft to bend and optimally oppose and seal against the native vessel.

SUMMARY OF THE INVENTION

The one embodiment of the invention is directed to an improved, modular, bifurcated stent graft having an integral support tube. In another embodiment, the invention is directed to a highly conformable stent graft with or without at least one portal for a side branch device (e.g. a stent graft).

One embodiment of the invention comprises a multi-lumen stent graft comprising: a primary lumen defined by a graft composed of an innermost tube with an opening and an outermost tube with an opening, said graft being supported by a primary stent; and a secondary lumen disposed between the innermost tube and outermost tube of said graft, wherein said secondary lumen is in fluid communication through said openings. In one embodiment, said secondary lumen comprises a secondary stent or stent assembly. In another embodiment, said secondary lumen can accept another smaller stent graft.

Another embodiment of the invention comprises a stent graft for implantation in a bifurcated body lumen having a main branch vessel and a side branch vessel, wherein the stent graft comprises: a graft, said graft composed of an innermost tube with an opening and an outermost tube with an opening, said graft extending along a longitudinal axis from a distal end to a proximal end and defining a main lumen extending therethrough, said graft being supported by a primary stent; and a secondary lumen disposed between the innermost tube and outermost tube of said graft, said secondary lumen portion positioned between the distal and proximal ends of said graft, wherein said secondary lumen is in fluid communication through said openings of said innermost and outermost tubes. In one embodiment, said primary stent is a self expanding stent.

Another embodiment of the invention comprises covering a first mandrel that comprises a groove and a back wall of said groove with an innermost polymeric tube; slitting said polymeric tube along said back wall of said groove; placing a second mandrel into said groove of the first mandrel and aligning said second mandrel with the back wall of the groove, deforming said innermost polymeric tube; placing an outermost polymeric tube over said inner most tube; and making an opening over said second smaller mandrel; wherein said outermost tube and innermost tube comprise a graft member.

Another embodiment of the invention comprises a graft being supported by a stent, wherein said stent comprise undulations each which comprise apices in opposing first and second directions, and a tape member, having first and second longitudinal edges, attached to said stent and to said graft such that the first tape edge substantially covers the apices in the first or the second direction of the each of the undulations, thus confining the apices in the first direction or second direction of the undulations to the graft and wherein the apices in the first or the second direction of the undulation are not confined relative to the graft. In one embodiment, said apices in the first direction are confined to the graft and the apices in second direction are not confined relative to the graft. In another embodiment, said apices in the second direction apices are confined to the graft and the apices in the first direction are not confined relative to the graft. In another embodiment, said graft forms circumferentially oriented unidirectional pleats where longitudinally compressed. In another embodiment, said apices in the first direction of said undulation are positioned under an adjacent pleat where compressed. In another embodiment, said stent is formed from a single continuous wire helical wrapped around said graft. In another embodiment, said stent is a self-expanding stent. In another embodiment, said stent is made from Nitinol. In another embodiment, said undulations have a sinusoidal shape. In another embodiment, said graft comprises polytetrafluoroethylene.

Additional features and advantages of the invention will be set forth in the description or may be learned by practice of the invention. These features and other advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention and are incorporated in and constitute a part of this specification, illustrate embodiments of the invention and together with the description serve to explain the principles of the invention.

In the drawings:

FIGS. 1B, 1C, 1D and 1E comprise a bifurcated stent graft, in which the main body comprises at least one side branch portal made from a portion of the main body graft.

FIGS. 2A and 2B depict perspective views of a mandrel used to construct a main body stent graft having an integral support tube.

FIGS. 3A and 3B depict perspective views of a mandrel used to construct a main body stent graft having an integral support tube and a secondary stent assembly.

DETAILED DESCRIPTION OF THE ILLUSTRATED EMBODIMENTS

One embodiment of the invention is directed to an improved, modular, bifurcated stent graft having an integral support tube. In another embodiment, the invention is directed to a highly conformable stent graft with or without at least one portal for a side branch device (e.g. a stent graft).

Figure 1A:
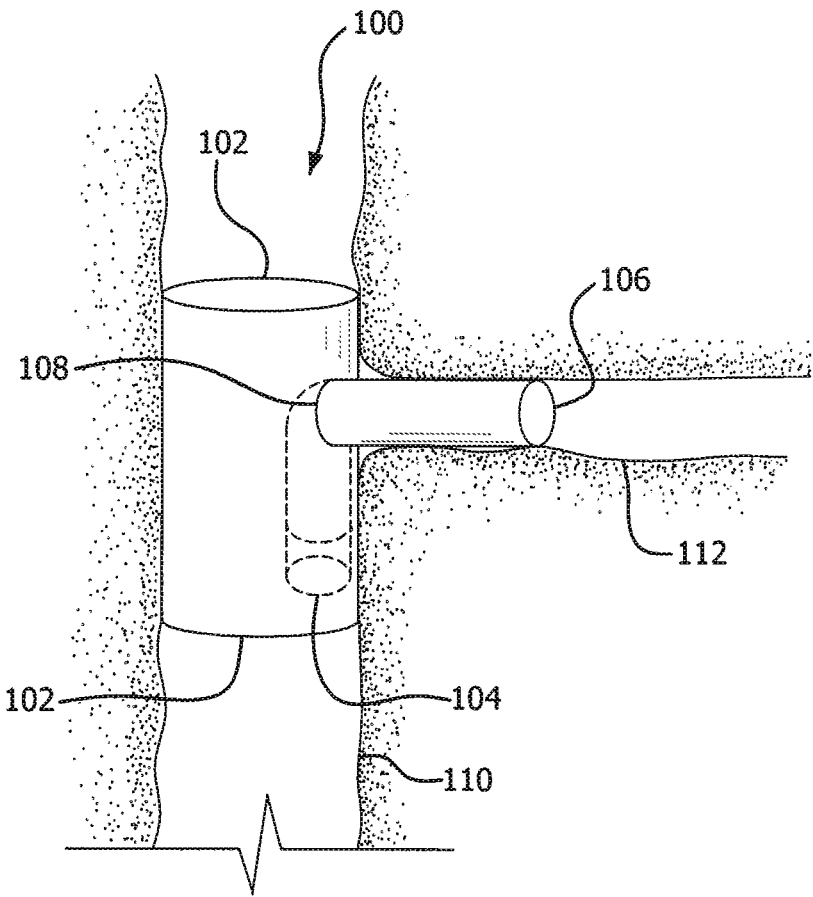
FIG. 1A is a perspective view of a modular, bifurcated stent graft having a main body stent, an internal support tube and attached side branch stent.

In general, most bifurcated stent grafts have an internal tube to create the bifurcation or a fenestration on the side of a stent graft in which another tube or stent graft is inserted. See, for example U.S. Pat. No. 6,645,242 to Quinn and U.S. Pat. No. 6,077,296 to Shokoohi. FIG. 1 is a perspective view of a general modular bifurcated stent graft 100 having a main body 102 with an internal tube 104. In general, most internal tubes (i.e. bifurcation tubes) are made by adding additional material that is formed into a tube or a bifurcation site and sewn and/or adhered to the internal side of the main body (usually the graft). The internal tube 104 is sized to engage and secure a side branch device 106, shown protruding from a main body portal 108. The main body 102 is shown implanted into a main vessel 110 with the side branch stent implanted into a branch vessel 112. The instant invention, as depicted in FIGS. 1B to 7, comprises a bifurcated stent graft, in which the main body comprises at least one side branch portal made from a portion of the main body graft wherein said at least a portion of said portal is integral with said graft and which at least a portion of said portal has no seams in the main blood flow surface of the graft and/or weakened areas due to non-continuous construction.

Figure 1D:
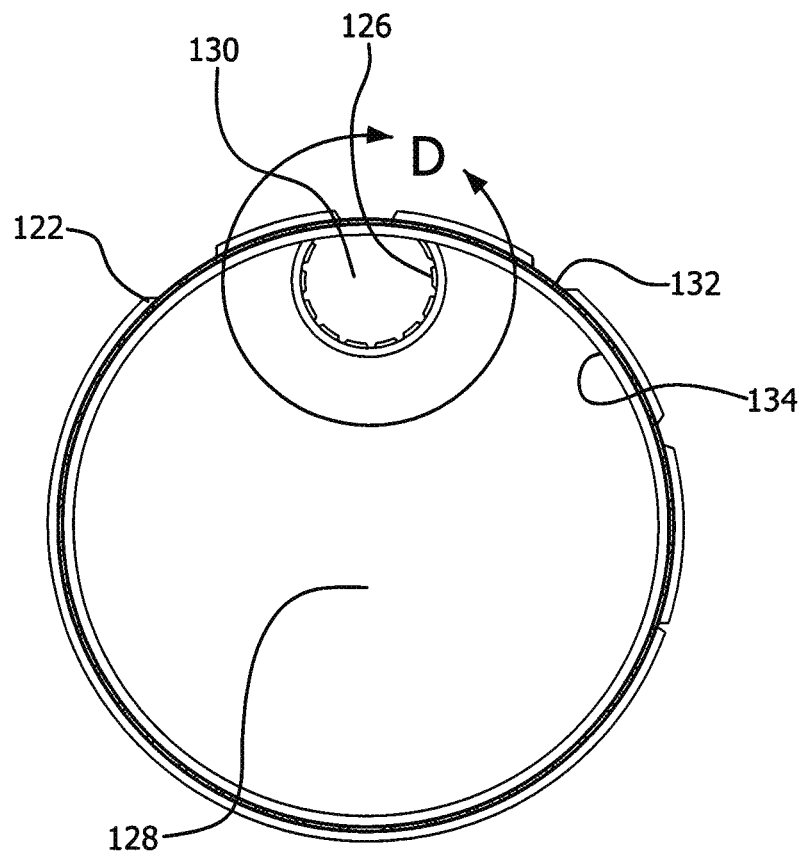
Figure 7:
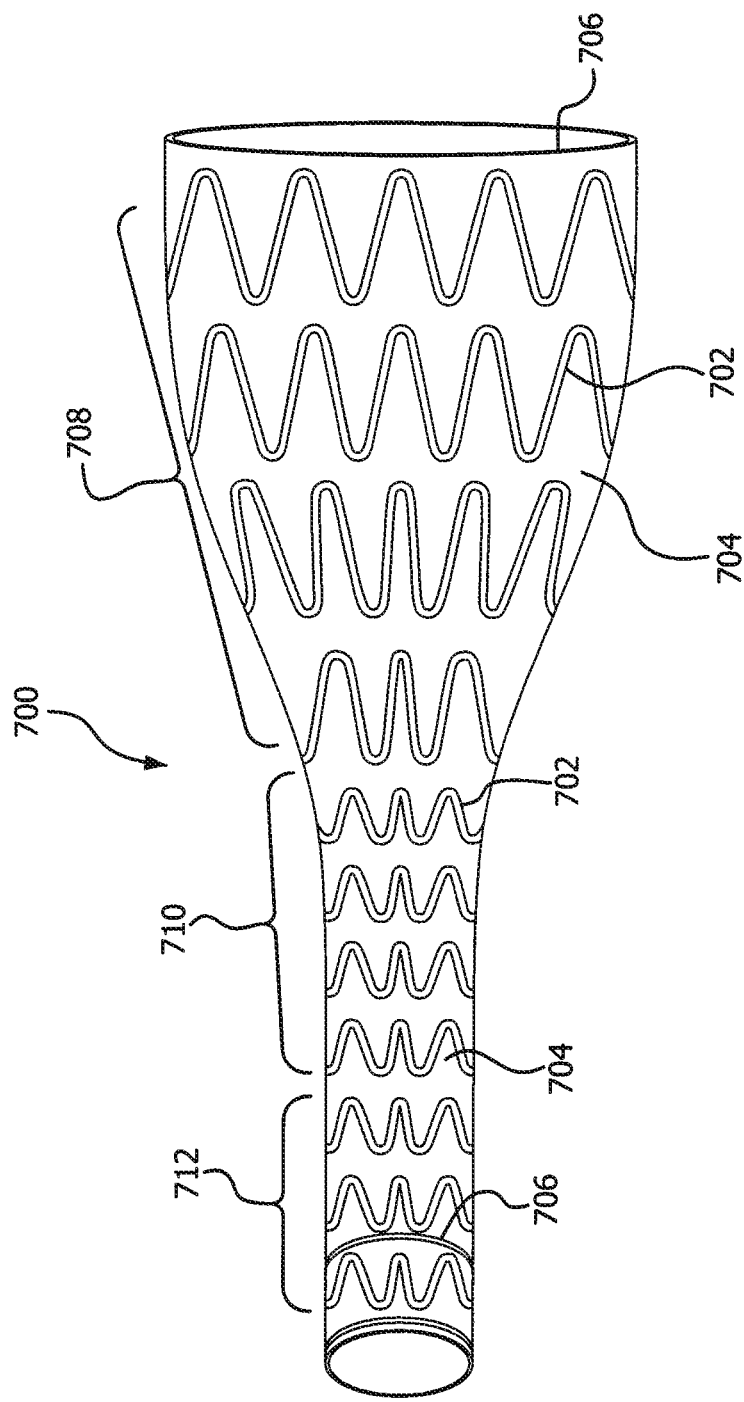
FIG. 7 is a perspective view of a side branch stent having three purpose built portions.

One embodiment of the invention is shown in FIGS. 1B to 1D. FIG. 1B is a top view of a bifurcated stent graft 120 having a primary stent (or main body stent) 122 with a side branch portal 124. Also depicted is a stent feature 121 which creates an area for the side branch portal. In this embodiment, said feature is called the "double W". In this embodiment, said "double W" helps support the side branch portal and prevents said portal from collapsing. In addition, this design creates a region for a side branch portal without creating a high strain region in the body winding pattern of the stent. Without being bound to a particular theory, one reason may be that the "double W" design does not rely on shorter amplitude struts that stiffen the frame and results in higher stains, which may cause fractures when the stent is stressed. The main body portal 124 is sized to engage and secure a side branch stent, one embodiment of which is depicted in FIG. 7, 700.

FIG. 1C is a side view with a partial longitudinal cross section of FIG. 1B. This Figure depicts primary lumen 128, a secondary lumen 130, an outermost tube 132, an innermost tube 134 and an optional secondary stent 126. Also depicted is the innermost tube opening 131.

FIG. 1D is a cross section of A-A in FIG. 1C. This Figure depicts primary stent 122, secondary stent 126, primary lumen 128, and secondary lumen 130. This Figure also depicts an outermost tube 132 and an innermost tube 134.

Figure 1E:
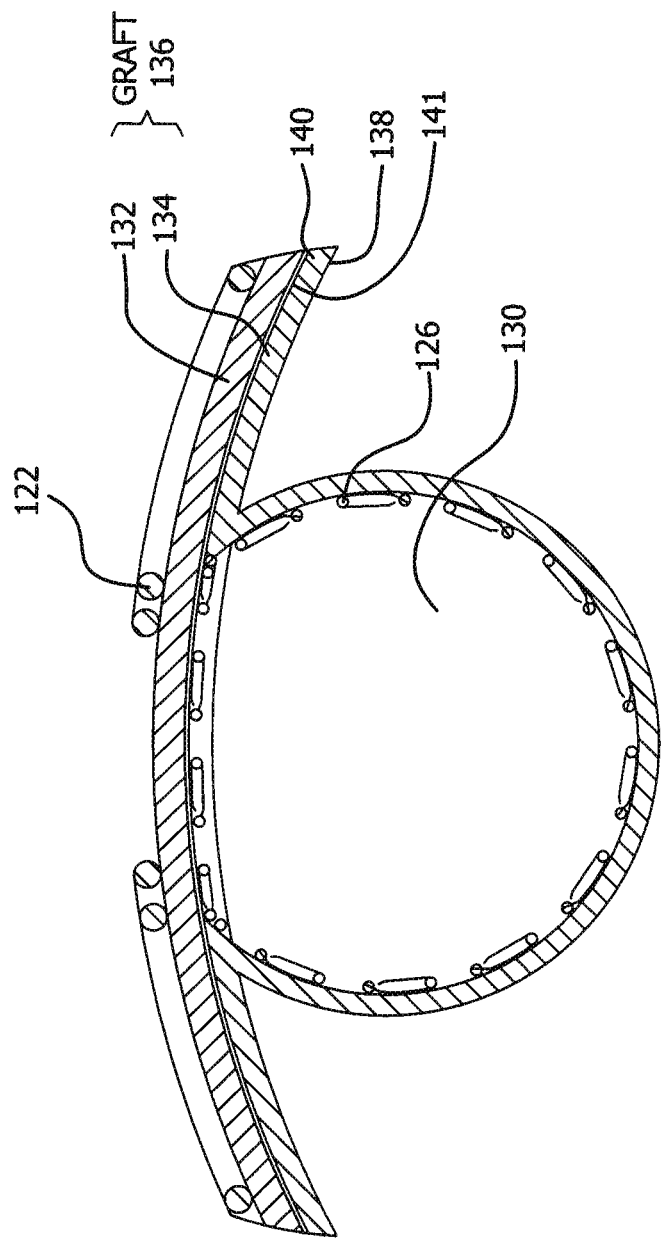

FIG. 1E is a close up of section D depicted on FIG. 1D. Thus, this Figure is a close up of the cross section of the side branch portal. This Figure depicts the primary stent 122, secondary stent 126, and secondary lumen 130. This Figure also depicts an outermost tube 132 and an innermost tube 134.

Graft 136 is composed of innermost tube 134 and outermost tube 132. Also depicted is the blood flow surface 138 (i.e. the internal graft surface), the outer surface of the innermost tube 140 and the inner surface of the outermost tube 141.

Thus, one embodiment of the invention, the bifurcated (multi-lumen) stent graft, comprises a primary lumen 128 defined by a graft 136 composed of an innermost tube 134 with an opening 131 and an outermost tube 132 with an opening 124, said graft being supported by a primary stent 122; and a secondary lumen 130 disposed between the innermost tube 132 and outermost tube 134 of said graft 136; wherein said secondary lumen is in fluid communication through said openings 131 and 124. In one embodiment, said secondary lumen 130 comprises a secondary stent 126 or stent assembly. As used herein, said secondary stent assembly is a secondary stent that is covered and may comprise additional features such as radiopaque markers. In another embodiment, said secondary lumen is disposed between the ends of the main stent graft or main body. In another embodiment, a portion of the said secondary stent or stent assembly abuts against a portion of the innermost tube 134. In another embodiment, said secondary stent or stent assembly abuts against a portion of graft 136. In another embodiment, a portion of said secondary stent or stent assembly lays on the outer surface of the innermost tube 140. In another embodiment, said secondary lumen is defined partially by the innermost tube and partially by the outermost tube. In another embodiment, said secondary lumen is defined partially by the outer surface of the innermost tube 140 and the inner surface of the outermost tube 141.

The graft of the stent graft of the invention may be made up of any material which is suitable for use as a graft in the chosen body lumen. Said graft can be composed of the same or different materials. Furthermore, said graft can comprise multiple layers of material that can be the same material or different material. Although the graft can have several layers of material, said graft may have a layer that is formed into a tube (innermost tube) and an outermost layer that is formed into a tube (outermost tube). For the purposes on this invention, the outermost tube does not comprise a tape layer that may be used to adhere a stent to a graft as described in more detail below. In one embodiment of the invention, said graft comprises an innermost tube and an outermost tube.

Many graft materials are known, particularly known are those that can be used as vascular graft materials. In one embodiment, said materials can be used in combination and assembled together to comprise a graft. The graft materials used in a stent graft can be extruded, coated or formed from wrapped films, or a combination thereof. Polymers, biodegradable and natural materials can be used for specific applications.

Examples of synthetic polymers include, but are not limited to, nylon, polyacrylamide, polycarbonate, polyformaldehyde, polymethylmethacrylate, polytetrafluoroethylene, polytrifluorochlorethylene, polyvinylchloride, polyurethane, elastomeric organosilicon polymers, polyethylene, polypropylene, polyurethane, polyglycolic acid, polyesters, polyamides, their mixtures, blends and copolymers are suitable as a graft material. In one embodiment, said graft is made from a class of polyesters such as polyethylene terephthalate including DACRON® and MYLAR® and polyaramids such as KEVLAR®, polyfluorocarbons such as polytetrafluoroethylene (PTFE) with and without copolymerized hexafluoropropylene (TEFLON® or GORE-TEX®), and porous or non-porous polyurethanes. In another embodiment, said graft comprises expanded fluorocarbon polymers (especially PTFE) materials described in British. Pat. Nos. 1,355,373; 1,506,432; or 1,506,432 or in U.S. Pat. Nos. 3,953,566; 4,187, 390; or 5,276,276, the entirety of which are incorporated by reference. Included in the class of preferred fluoropolymers are polytetrafluoroethylene (PTFE), fluorinated ethylene propylene (FEP), copolymers of tetrafluoroethylene (TFE) and perfluoro (propyl vinyl ether) (PFA), homopolymers of polychlorotrifluoroethylene (PCTFE), and its copolymers with TFE, ethylene-chlorotrifluoroethylene (ECTFE), copolymers of ethylene-tetrafluoroethylene (ETFE), polyvinylidene fluoride (PVDF), and polyvinyfluoride (PVF). Especially preferred, because of its widespread use in vascular prostheses, is ePTFE. In another embodiment, said graft comprises a combination of said materials listed above. In another embodiment, said graft is substantially impermeable to bodily fluids. Said substantially impermeable graft can be made from materials that are substantially impermeable to bodily fluids or can be constructed from permeable materials treated or manufactured to be substantially impermeable to bodily fluids (e.g. by layering different types of materials described above or known in the art). In another embodiment, said outermost tube comprises ePTFE. In another embodiment, said innermost tube comprises ePTFE. In another embodiment, said innermost and outermost tube comprises ePTFE film that has been wrapped into a tube. In another embodiment, said secondary stent is covered with any of the material disclosed herein or known in the art. In another embodiment, the secondary stent covering comprises ePTFE.

Additional examples of graft materials include, but are not limited to, vinylidinefluoride/hexafluoropropylene hexafluoropropylene (HFP), tetrafluoroethylene (TFE), vinylidenefluoride, 1-hydropentafluoropropylene, perfluoro (methyl vinyl ether), chlorotrifluoroethylene (CTFE), pentafluoropropene, trifluoroethylene, hexafluoroacetone, hexafluoroisobutylene, fluorinated poly(ethylene-co-propylene (FPEP), poly(hexafluoropropene) (PHFP), poly(chlorotrifluoroethylene) (PCTFE), poly(vinylidene fluoride (PVDF), poly(vinylidene fluoride-co-tetrafluoroethylene) (PVDF-TFE), poly(vinylidene fluoride-co-hexafluoropropene) (PVDF-HFP), poly(tetrafluoroethylene-co-hexafluoropropene) (PTFE-HFP), poly(tetrafluoroethylene-co-vinyl alcohol) (PTFE-VAL), poly(tetrafluoroethylene-co-vinyl acetate) (PTFE-VAC), poly(tetrafluoroethylene-co-propene) (PT-FEP) poly(hexafluoropropene-co-vinyl alcohol) (PHFP-VAL), poly(ethylene-co-tetrafluoroethylene) (PETFE), poly (ethylene-co-hexafluoropropene) (PEHFP), poly(vinylidene fluoride-co-chlorotrifluoroe-thylene) (PVDF-CTFE), and combinations thereof, and additional polymers and copolymers described in U.S. Publication 2004/0063805, incorporated by reference herein in its entirety for all purposes. Additional polyfluorocopolymers include tetrafluoroethylene (TFE)/perfluoroalkylvinylether (PAVE). PAVE can be perfluoromethylvinylether (PMVE), perfluoroethylvinylether (PEVE), or perfluoropropylvinylether (PPVE), as essentially described in U.S. Publication 2006/0198866 and U.S. Pat. No. 7,049,380, both of which are incorporated by reference herein for all purposes in their entireties. Other polymers and copolymers include, polylactide, polycaprolacton-glycolide, polyorthoesters, polyanhydrides; poly-aminoacids; polysaccharides; polyphosphazenes; poly(ether-ester) copolymers, e.g., PEO-PLLA, or blends thereof, polydimethyl-sioxane; poly(ethylene-vingylacetate); acrylate based polymers or copolymers, e.g., poly(hydroxyethyl methylmethacrylate, polyvinyl pyrrolidinone; fluorinated polymers such as polytetrafluoroethylene; cellulose esters and any polymer and copolymners described in U.S. Publication 2004/0063805, incorporated by reference herein in its entity.

Figure 8:
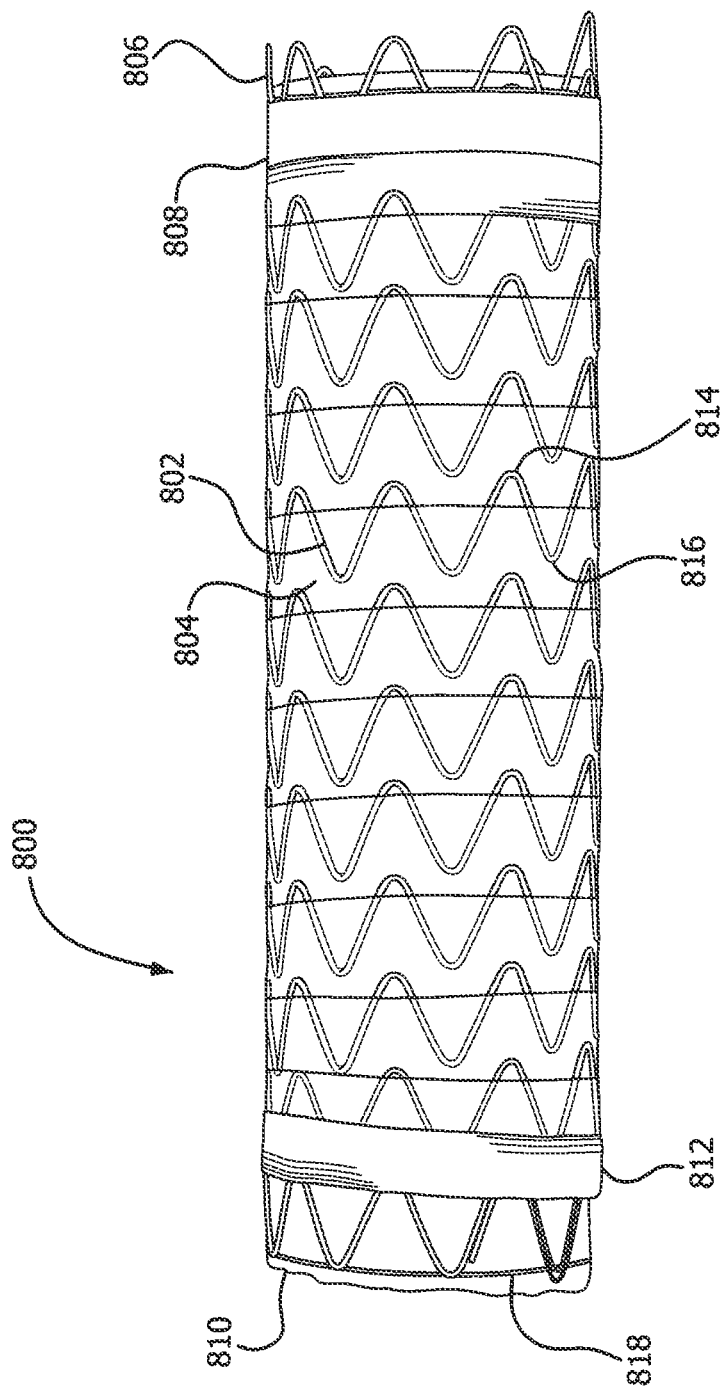
FIG. 8 depicts a fully extended stent graft.

Said stents of the instant intention are generally cylindrical and comprise helically arranged undulations having plurality of helical turns. The undulations preferably are aligned so that they are "in-phase" with each other as shown in FIG. 8. More specifically, undulations comprise apices in opposing first 814 and second 816 directions. When the undulations are in-phase, apices in adjacent helical turns are aligned so that apices can be displaced into respective apices of a corresponding undulation in an adjacent helical turn. In one embodiment, said undulations have a sinusoidal shape. In another embodiment, said undulations are U shaped. In another embodiment, said undulations are V shaped. In another embodiment, said undulations are ovaloid shaped. These shapes are fully described in U.S. Pat. No. 6,042,605, FIGS. 14A-E. U.S. Pat. No. 6,042,605 is incorporated by reference herein in its entirety for all purposes.

In another embodiment of the invention, said stent can be fabricated from a variety of biocompatible materials including commonly known materials (or combinations of materials) used in the manufacture of implantable medical devices. Typical materials include 316L stainless steel, cobalt-chromium-nickel-molybdenum-iron alloy ("cobalt-chromium"), other cobalt alloys such as L605, tantalum, Nitinol, or other biocompatible metals. In one embodiment, said stent graft is a balloon expandable stent graft. In another embodiment, said stent graft is a self-expanding stent graft. In another embodiment, said stent is a wire wound stent. In another embodiment, said wire wound stent comprise undulations.

The wire wound stent can be constructed from a reasonably high strength material, i.e., one which is resistant to plastic deformation when stressed. In one embodiment, the stent member comprises a wire which is helically wound around a mandrel having pins arranged thereon so that the helical turns and undulations can be formed simultaneously, as described below. Other constructions also may be used. For example, an appropriate shape may be formed from a flat stock and wound into a cylinder or a length of tubing formed into an appropriate shape or laser cutting a sheet of material. In another embodiment, said stent is made from a super-elastic alloy. There are a variety of disclosures in which super-elastic alloys such as nitinol are used in stents. See for example, U.S. Pat. No. 4,503,569, to Dotter; U.S. Pat. No. 4,512,338, to Balko et al.; U.S. Pat. No. 4,990,155, to Wilkoff; U.S. Pat. No. 5,037,427, to Harada, et al.; U.S. Pat. No. 5,147,370, to MacNamara et al.; U.S. Pat. No. 5,211,658, to Clouse; and U.S. Pat. No. 5,221,261, to Termin et al.

A variety of materials variously metallic, super elastic alloys, such as Nitinol, are suitable for use in these stents. Primary requirements of the materials are that they be suitably springy even when fashioned into very thin sheets or small diameter wires. Various stainless steels which have been physically, chemically, and otherwise treated to produce high springiness are suitable as are other metal alloys such as cobalt chrome alloys (e.g., ELGILOY®), platinum/tungsten alloys, and especially the nickel-titanium alloys generically known as "nitinol".

Nitinol is especially preferred because of its "super-elastic" or "pseudo-elastic" shape recovery properties, i.e., the ability to withstand a significant amount of bending and flexing and yet return to its original form without permanent deformation. These metals are characterized by their ability to be transformed from an austenitic crystal structure to a stress-induced martensitic structure at certain temperatures, and to return elastically to the austenitic shape when the stress is released. These alternating crystalline structures provide the alloy with its super-elastic properties. These alloys are well known but are described in U.S. Pat. Nos. 3,174,851; 3,351,463; and 3,753,700.

Other suitable stent materials include certain polymeric materials, particularly engineering plastics such as thermotropic liquid crystal polymers ("LCP's"). These polymers are high molecular weight materials which can exist in a so-called "liquid crystalline state" where the material has some of the properties of a liquid (in that it can flow) but retains the long range molecular order of a crystal. The term "thermotropic" refers to the class of LCP's which are formed by temperature adjustment. LCP's may be prepared from monomers such as p,p'-dihydroxy-polynuclear-aromatics or dicarboxy-polynuclear-aromatics. The LCP's are easily formed and retain the necessary interpolymer attraction at room temperature to act as high strength plastic artifacts as are needed as a foldable stent. They are particularly suitable when augmented or filled with fibers such as those of the metals or alloys discussed below. It is to be noted that the fibers need not be linear but may have some preforming such as corrugations which add to the physical torsion enhancing abilities of the composite.

Another embodiment of the invention comprises a stent graft for implantation in a bifurcated body lumen having a main branch vessel and a side branch vessel, wherein the stent graft comprises: a graft, said graft composed of an innermost tube with an opening and an outermost tube with an opening, said graft extending along a longitudinal axis from a distal end to a proximal end and defining a main lumen extending therethrough, said graft being supported by a primary stent; and a secondary lumen disposed between the innermost tube and outermost tube of said graft, said secondary lumen portion positioned between the distal and proximal ends of said graft, said secondary lumen is in fluid communication through said openings of said innermost and outermost tubes. In one embodiment, said primary stent is a self expanding stent. In another embodiment, said self expanding stent comprises a titanium-nickel alloy. In another embodiment, said stent comprises a single continuous wire helically wrapped around said graft. In another embodiment, wherein said single continuous wire comprises undulations. In another embodiment, said undulating wire comprises multiple turns of said undulations, and each turn of said undulating wire comprises multiple apexes, with undulation in one turn generally in-phase with undulation in an adjacent turn. In another embodiment, said undulations are U shaped. In another embodiment, said undulations are V shaped. In another embodiment, said undulations are ovaloid shaped. In another embodiment, said undulations are sinusoidal shaped. In another embodiment, said stent is attached to said graft. In another embodiment, said stent is attached to said graft by a ribbon or tape. In another embodiment, said ribbon or tape is adhered to a portion of said stent and a portion of said graft. In another embodiment, said ribbon or tape is arranged in a helical configuration with multiple turns. In another embodiment, said ribbon or tape is arranged in a helical configuration with multiple turns, each turn being spaced from an adjacent turn. In another embodiment, said spacing between said turns is uniform. In another embodiment, said ribbon covers a portion of said undulation. In another embodiment, said stent comprises undulations each which comprise an apex portion and a base portion and said ribbon or tape is attached to said stent such that the ribbon is placed along to the base portion of the each of the undulations thus confining the base portion of the undulations to the graft and wherein the apex portion of the undulation is not confined.

At least one method of making a main body stent graft having an integral support tube is described in FIG. 2 through FIG. 7.

FIG. 2A is a perspective view of a metallic mandrel 200 having a slot or groove 202 formed into one end of the mandrel. The groove 202 terminates into a back wall 204. As shown in perspective view FIG. 2B, an inner tube 206 is slip-fit over the mandrel 200, covering a portion of the mandrel groove 202. An inner tube can comprise any biocompatible polymer that is deformable (to allow a subsequent insertion of a side branch stent) and can be extruded, coated or formed from wrapped films. Suitable materials used for the inner tube may include, but are not limited to, any of the material described above, any other biocompatible material commonly known in the art or a combination thereof.

FIG. 3A is a perspective view of the mandrel 200 covered by the inner tube 206. The inner tube is cut, forming a slit 300 at the back wall 204 of the mandrel groove 202. As shown in FIG. 3B, a side branch or secondary stent assembly 302 is aligned to the mandrel groove 202, mandrel back wall 204 and inner tube slit 300. A first support segment (subsequently described) is placed into the secondary stent assembly and the secondary stent assembly 302 (with the first support segment) is then inserted into the mandrel groove 202, deforming the inner tube 206 into the mandrel groove. The back wall 204 defines the opening in the innermost tube (131, FIG. 1E)

Figure 4A:
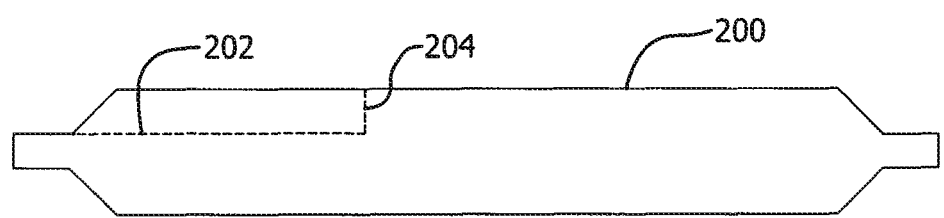
FIGS. 4A and 4B depict schematic side views of a mandrel used to construct a main body stent graft having an integral support tube and a secondary stent assembly.
Figure 4B:
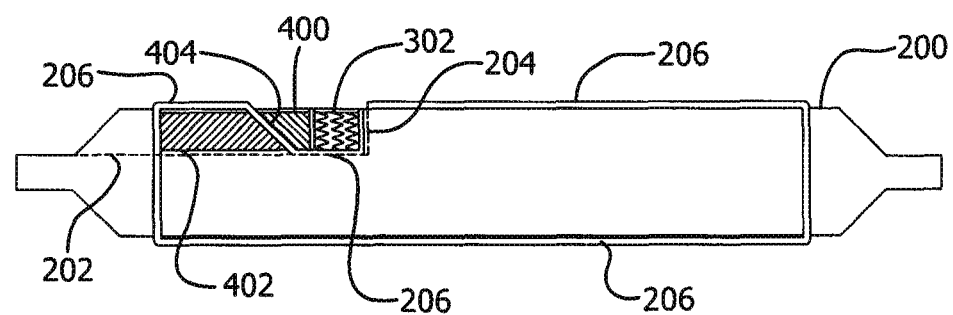

To control the deformed shape of the inner tube, support segments are placed into the secondary stent assembly and into the mandrel groove, as depicted in FIGS. 4A and 4B. Shown in FIG. 4A is a side view schematic of the mandrel 200, the groove 202 and the groove back wall 204. Shown in FIG. 4B is a side view schematic of the mandrel 200, mandrel groove 202 and inner tube 206. The secondary stent assembly 302 has been placed over a first support segment 400 having an end formed to mate to the mandrel groove back wall 204. The opposing end of the first support segment has a tapered or angulated wall as depicted in FIG. 4B. A second support segment 402 is placed into the mandrel groove 202 under the inner tube 206. The second support structure can have an angulated wall that mates with the angulated wall of the first support structure, although it is not required for the second support structure to have an angulated wall. One of the purposes of this second support structure to keep first support segment 400 in place during manufacturing. The inner tube 206 is shown deformed into the mandrel groove 202. The inner tube 206 is also shown having a tapered, beveled or angulated wall portion 404 formed by the angulated wall of the support segment 400.

To further strengthen the inner tube (FIG. 3A, 206), additional sheet or film layers may be added onto the inner tube prior to the insertion of the secondary stent assembly. For example a square/rectangle shaped thin film sheet having a high degree of bi-axial strength may be placed onto the inner tube 206 and aligned to the mandrel groove. The sheet can be dimensioned to be wider than the mandrel groove width and have a length approximating the mandrel groove length. This strengthening layer will then be deformed into the mandrel groove, providing additional support to the inner tube/secondary stent assembly. Multiple strengthening layers may be combined to enhance the properties of the inner tube. Suitable materials used for strengthening layers may include, but are not limited to, any of the material described above, any other biocompatible material commonly known in the art or a combination thereof.

Although the above methods describe the making of a bifurcated stent graft with only one portal, additional portals can also be made using similar methods describe above. Thus, another embodiment of the invention comprises a stent graft with at least two portals. In another embodiment, said stent graft of the invention comprises three, four, five, six or seven portals. Such a stent graft may be useful for, inter alia, implanting a stent graft in the abdominal aorta where the renal arteries branch off. In addition, due to the stent graft of the invention being highly conformable, see below, said stent graft of the invention with three portals can be placed in the arch of the aorta without blocking blood flow to the left subclavian artery, left common carotid artery and the bachiocephalic artery. In another embodiment, said several portals can be placed where desired longitudinally along the stent and/or circumferentially around the stent. A person of skill in the art can design said portals at any region in the vasculature.

At least one method of making a secondary stent assembly is outlined in FIGS. 5A through 5D. As shown in side view FIGS. 5A and 5B, a polymeric tube 502 is slip-fit onto a mandrel 500. An undulating wire can be formed into a ring stent 506 by winding the wire onto a mandrel with protruding pins. The diameters of the mandrel and pins along with the locations of the pins dictate the final configuration of the ring stent. After the wire is wound onto the mandrel, the mandrel and wire are heat treated and quenched to set the shape of the stent. The wire is then removed from the mandrel. The ends of the wire are joined together with a section of polymeric heat shrink tubing, forming ring stent 506. Other methods can be used to make the secondary stent (e.g. laser cutting). One or more of these ring stents 506 are then placed onto the polymeric tube 502. Optional radiopaque marker bands 504 are then placed onto the polymeric tube 502. The wire or metal tube used to make the secondary stent is described above. In one embodiment, said secondary stent comprises Nitinol.

Figure 5A:
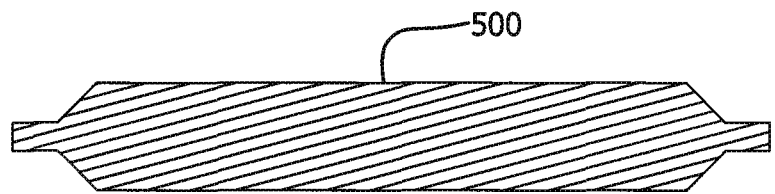
FIGS. 5A, 5B, 5C and 5D are side views of a mandrel and stent fabrication process.
Figure 5B:
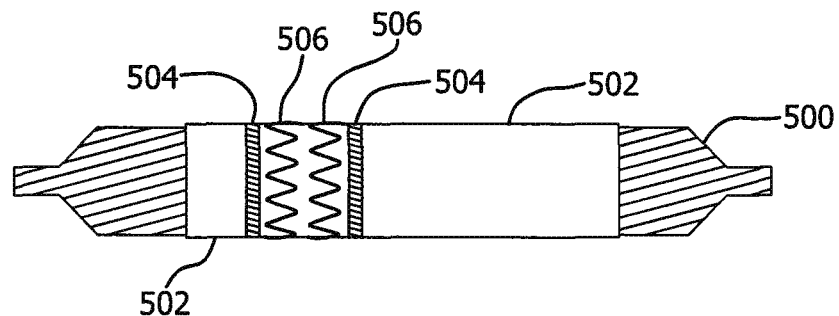
Figure 5C:
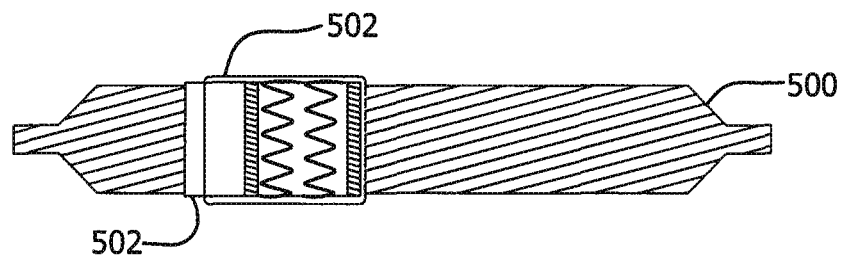
Figure 5D:
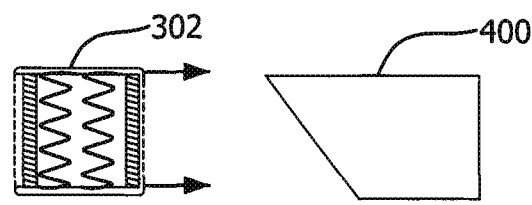

Next, as shown in FIG. 5C, one end of the polymeric tube 502 is inverted and drawn over the wire ring stents 506 and optional radiopaque marker bands 504. The mandrel, polymeric tube, ring stents and radiopaque bands are then heat treated to bond the components together into a stent assembly. The assembly is removed from the mandrel and trimmed to length, forming a secondary stent assembly 302 as shown in FIG. 5D. The secondary stent assembly is then placed onto a first support segment 400. Radiopaque markers include, but are not limited to gold, platinum, platinum-tungsten, palladium, platinum-iridium, rhodium, tantalum, or alloys or composites of these metals.

As previously described in FIG. 4B, the secondary stent (or secondary stent assembly) and the first support assembly are then inserted into the mandrel groove 202, deforming the inner tube 206 into the mandrel groove. The assembly shown in FIG. 4B is then covered with an outer polymeric tube. As described herein, said tube can be can be extruded, coated or formed from wrapped films.

The assembly is heat treated to join the inner tube to the outer tube. A side branch portal or opening (FIG. 1, item 108) is formed as described above. A primary wire stent is then formed by winding a wire onto a mandrel with protruding pins. The wire is heat treated to set the shape of the wire with a process similar to that used to form the secondary stent (FIG. 5B). The primary stent is then placed over the outer polymeric tube and overwrapped with a polymeric film. The assembly is then heat treated to bond the components together.

Methods of attaching a stent to a graft are known in the art. One embodiment comprises a coupling member that is generally a flat ribbon or tape having at least one generally flat surface. In another embodiment of the invention, the tape member is made from expanded PTFE (ePTFE) coated with an adhesive. In another embodiment, said adhesive is a thermoplastic adhesive. In another embodiment, said thermoplastic adhesive is fluorinated ethylene propylene (FEP). In this embodiment, the FEP-coated side faces toward and contacts the exterior surface of the stent and graft, thus attaching the stent to the graft. Although a particular tape member configuration and pattern has been illustrated and described, other configuration and/or patterns may be used without departing from the scope of the present invention. Materials and method of attaching a stent to the graft is discussed in U.S. Pat. No. 6,042,602 to Martin, incorporated by reference herein for all purposes.

Figure 6:
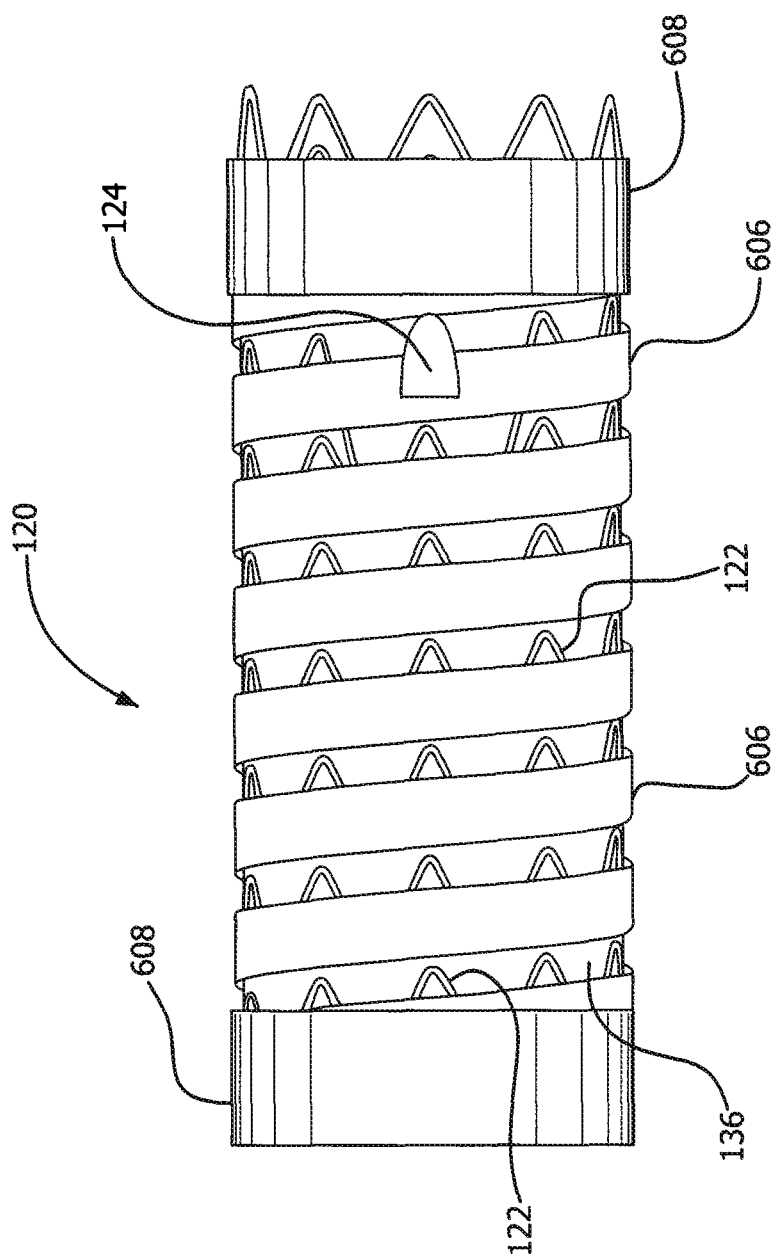
FIG. 6 is a top view of a bifurcated stent graft with a side branch portal.

FIG. 6 depicts a top view of a bifurcated stent graft 120 with a side branch portal 124. In this embodiment, the stent graft comprises a helically formed undulating wire primary stent 122. The primary stent 122 is joined to graft 136 by a film wrapping 606, as described above. The stent has film wrapped sealing cuffs 608 on the two opposing ends of the stent graft assembly 120. Such methods of assembly are generally disclosed in, for example, U. S. Pat. No. 6,042,605 issued to Martin, et al., U.S. Pat. No. 6,361,637 issued to Martin, et al. and U.S. Pat. No. 6,520,986 issued to Martin, et al. incorporated by reference herein for all purposes.

A side branch stent graft would ideally have a distal portion having a high degree of radial stiffness to allow apposition and sealing against a vessel wall. The side branch stent would also have a mid-portion that is highly flexible and highly fatigue resistant to the pulsatile and cyclic loading imparted by the native vessels. The side branch stent would also have a proximal portion that is deployed into the main body stent. This proximal portion of the side branch stent requires a high degree of radial stiffness in order to dock and seal properly into the main body portal.

Shown in FIG. 7 is one embodiment of a side branch stent graft 700, comprising a wire wound metallic stent 702, a graft covering 704 and radiopaque marker bands 706. The side branch stent has a distal portion 708, a mid-portion 710 and a proximal portion 712. The distal portion 708 has a high degree of radial stiffness to allow apposition and sealing against a branch vessel wall (FIG. 1, 112). The mid-portion 710 is highly flexible and highly fatigue resistant to the pulsatile and cyclic loading imparted by the native vessels. The proximal portion 712 that is deployed into the main body stent (FIG. 1, 102), has a high degree of radial stiffness in order to dock and seal properly into the main body portal and can resist compression and remain patent if an additional device deployment is used (e.g. an extender).

The process used to manufacture a side branch stent graft 700, can be used to fabricate the stent graft assembly (FIG. 6, 120) as defined above. Such methods of assembly are generally disclosed in, for example, U.S. Pat. No. 6,042,605 issued to Martin, et al., U.S. Pat. No. 6,361,637 issued to Martin, et al. and U.S. Pat. No. 6,520,986 issued to Martin, et al. The stiffness, radial strength, flexibility and fatigue life of a side branch stent can be controlled by the stent wire properties, wound pattern geometries of the wire, graft properties and wire to graft attachment configurations. For example in FIG. 7, the distal portion 708 of the side branch stent 700 has an undulating wire pattern with relatively large undulation amplitude. The undulations are also spaced relatively far apart. In comparison, the mid-portion 710 of the side branch stent has an undulating wire pattern with relatively small undulation amplitude. The undulations are also spaced relatively far apart. Finally, the proximal portion 712 that is deployed into the main body stent (FIG. 1, 102), has an undulating wire pattern with relatively large undulation amplitude. The undulations are also spaced relatively close to the adjacent wires.

Methods of joining the side branch stent graft to the main-stent graft are known. These include, but are not limited to friction fits, hooks, and barbs and/or raised stent apices. Additional methods are disclosed in U.S. Publication 2009/0043376 to Hamer and Zukowski, incorporated by reference herein in its entirety for all purposes.

The stent graft may be delivered percutaneously, typically through the vasculature, after having been folded to a reduced diameter. Once reaching the intended delivery site it is expanded to form a lining on the vessel wall. In one embodiment the stent graft is folded along its longitudinal axis and restrained from springing open. The stent graft is then deployed by removing the restraining mechanism, thus allowing the graft to open against the vessel wall. The stent grafts of this invention are generally self-opening once deployed. If desired, an inflatable balloon catheter or similar means to ensure full opening of the stent graft may be used under certain circumstances. In another embodiment, said stent graft is a balloon expandable stent. The side branch can also be delivered percutaneously after having been folded to a reduced diameter.

The stent graft of the invention may comprise at least one or two radiopaque markers, to facilitate proper positioning of the stent graft within the vasculature. Said radiopaque markers can be used to properly align the stent graft both axially and rotationally to confirm that the side portal is properly aligned. Said radio markers include, but are not limited to gold, platinum, platinum-tungsten, palladium, platinum-iridium, rhodium, tantalum, or alloys. Alternatively, provided that the delivery catheter design exhibits sufficient torque transmission, the rotational orientation of the graft maybe coordinated with an indexed marker on the proximal end of the catheter, so that the catheter may be rotated to appropriately align the side branch(es). Additional methods of delivering the bifurcated stent graft of the invention and an associated side branch are disclosed in U.S. Publication 2008/0269866 to Hamer and Johnson and U.S. Publication 2008/0269867 to Johnson, both of which are incorporated by reference herein in their entirety for all purposes.

Another embodiment of the invention comprises a highly conformable stent graft that can conform to highly tortuous sections of a native vessel. Said stent graft may optionally encompass at least one side branch portal.

Referring to FIG. 8, the highly conformable stent graft of the invention 800 generally includes a graft 804, a stent 802 and a tape member (1406, FIG. 14) for coupling the stent and graft member together and is highly conformable. Preferably, the stent and graft are coupled together so that they are generally coaxial.

Figure 9:
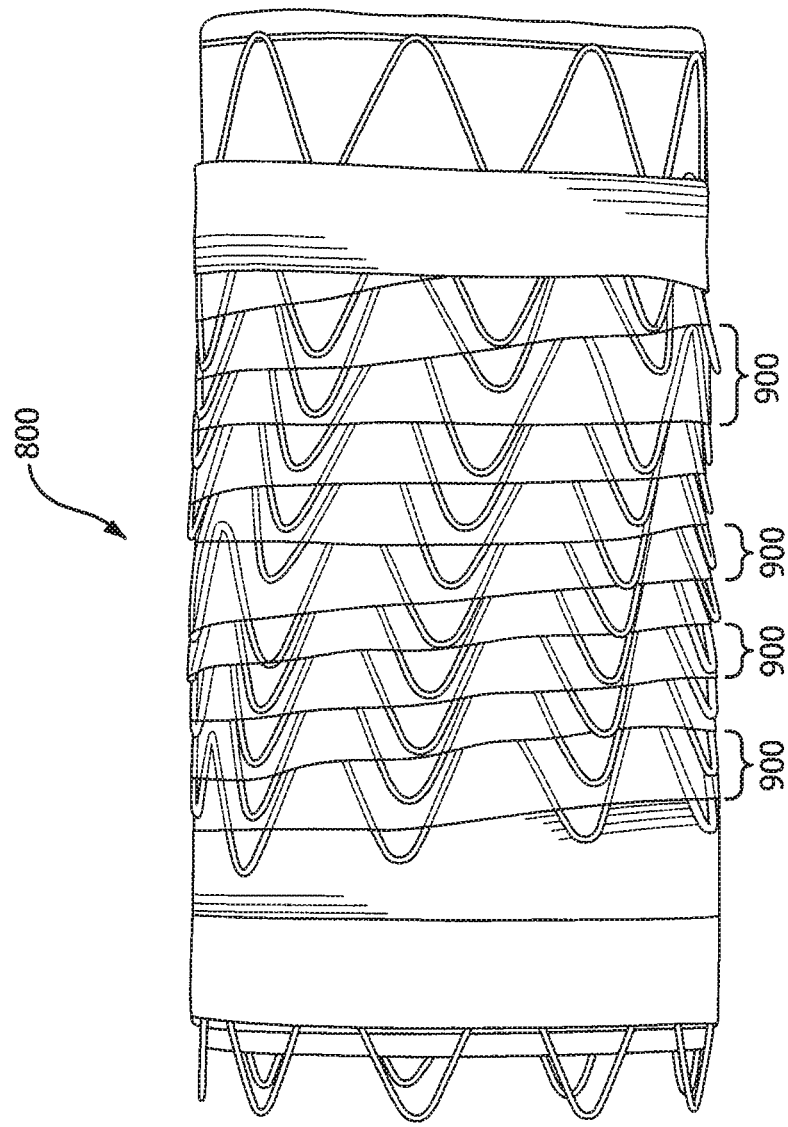
FIG. 9 depicts a flexible stent graft in a state of full longitudinal compression, wherein the unidirectional pleats are formed around the full circumference of the stent graft.

In one embodiment of the invention, the highly conformable stent graft 800 has a helically formed wire stent 802 surrounding a graft 804. The wire form stent has opposing first 814 and second 816 direction apices. The stent graft 800 has a first end portion 806 optionally comprising a sealing cuff 808. Similarly, the stent graft 800 has a second end portion 810 optionally comprising a second sealing cuff 812 (folded back for illustration purposes) and a radiopaque marker 818. As depicted in FIG. 9, the flexible stent graft 800 has unidirectional pleats 900 that are formed upon longitudinal compression. In one embodiment, said stent graft of the invention has at least one portal between the ends of said stent graft of the invention for the introduction of a side branch device. In another embodiment, said side branch device is a stent graft.

FIG. 9 shows a flexible stent graft 800 in a state of longitudinal compression, wherein the unidirectional pleats 900 are formed around the full circumference of the stent graft 800.

Figure 10A:
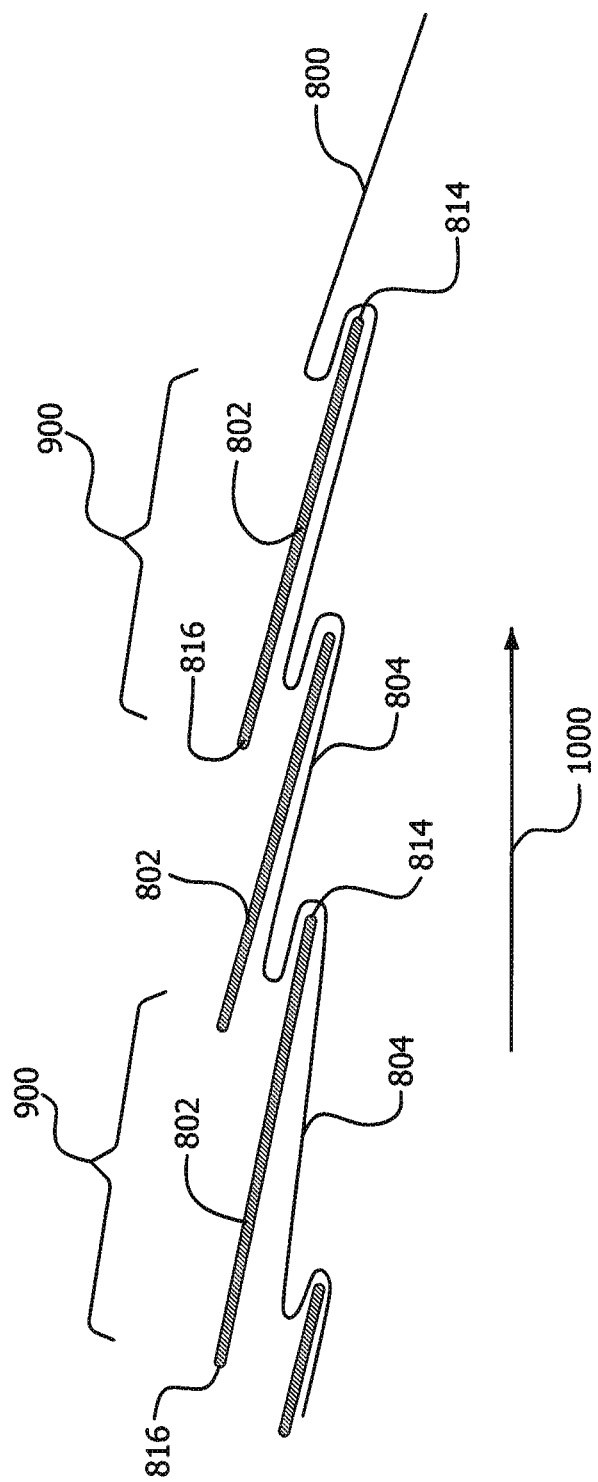
FIGS. 10A and B depict a partial cross-sectional view of one wall of the stent graft, taken along cross-sectional plane 3-3 of FIG. 8, illustrating the unidirectional pleating of the compressed stent graft.
Figure 10B:
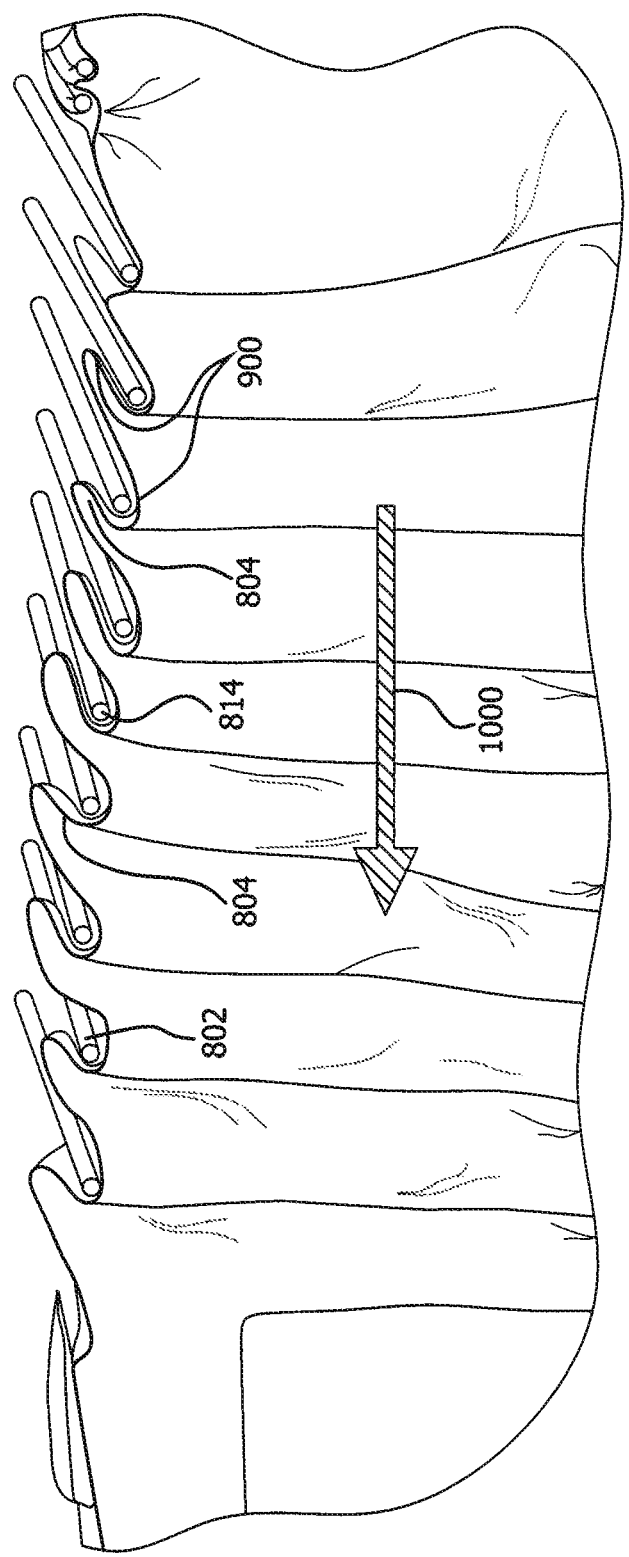

FIG. 10A is a partial longitudinal cross-sectional view of one wall of the stent graft 800, taken along cross-sectional plane 3-3 of FIG. 9, illustrating the unidirectional pleating of the compressed stent graft 800. The unidirectional pleats have a common orientation and are all bent in the same direction. The wire stent 802 is shown with opposing first directional apices 814 tucked under an adjacent folded portion of the graft material 804, forming a unidirectional pleat 900. The arrow 1000 indicates a preferred blood flow direction as "going with the pleats" to minimize flow disruption and turbulence. FIG. 10B is a long cross-sectional view similar to that of FIG. 10A, showing unidirectional pleats 900, along with a preferred blood flow direction 1000.

Figure 11:
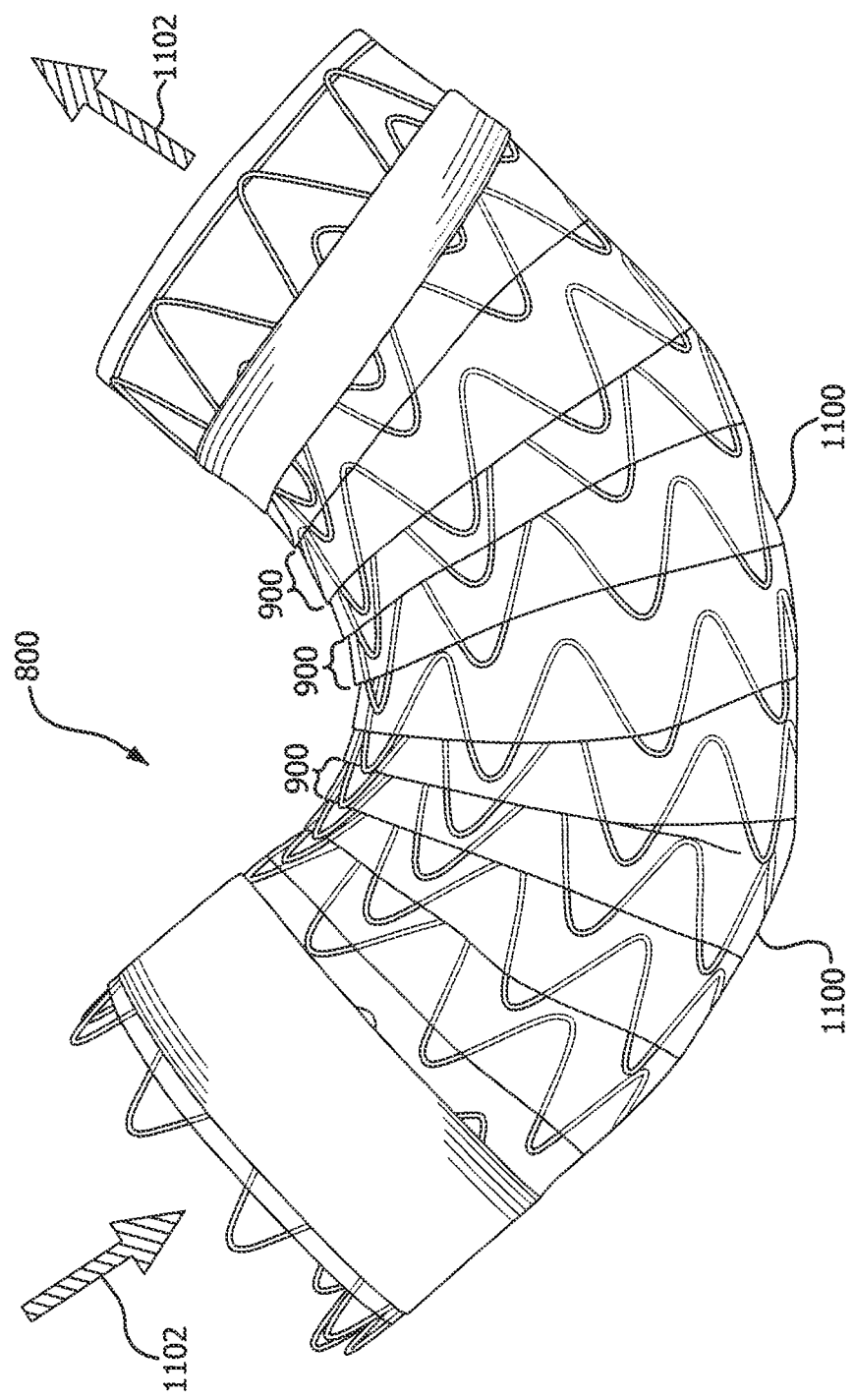
FIG. 11 depicts a flexible stent graft a state of partial longitudinal compression (or in a bent shape), wherein the unidirectional pleats are formed on a portion of the stent graft circumference (or on the inner meridian) and the outer meridian has un-pleated or straight graft portions.

FIG. 11 shows a flexible stent graft 800 in a bent shape that imparts compression to the wall of the graft along the inner meridian of the bend (i.e. partial longitudinal compression) wherein the unidirectional pleats 900 are formed on a portion of the stent graft circumference (or the inner meridian). The outer meridian has un-pleated or straight graft portions 1100. The arrow 1102 indicates a preferred blood flow direction as previously shown in FIG. 10.

One embodiment of the invention comprises a graft being supported by a stent, wherein said stent comprises undulations each which comprise apices in opposing first and second directions, and a tape member, having first and second longitudinal edges, attached to said stent and to said graft such that the first tape edge substantially covers the apices in the first or the second direction of the each of the undulations, thus confining the apices in the first or the second direction of the undulations to the graft and wherein the apices in the first or the second direction of the undulation are not confined relative to the graft. In one embodiment, said apices in the first direction apices are confined to the graft and the second direction apices are not confined relative to the graft. In another embodiment, said apices in the second direction apices are confined to the graft and the first direction apices are not confined relative to the graft. In another embodiment, said graft forms circumferentially oriented unidirectional pleats where longitudinally compressed. In another embodiment, said confined apices (either in the first direction or second direction) of said undulation are positioned under an adjacent pleat when compressed. The term "confined apices" means that the apices are attached to the graft by either a tape member or attached by another method known in the art. In another embodiment, said confined apices are positioned under an adjacent pleat thereby covering about 1%, about 2%, about 3%, about 4%, about 5%, about 10%, about 20%, about 30%, about 40%, about 50% about 60%, about 70%, about 80% of undulation height 1312 (FIG. 13) of the apices in the first direction. Depending on the method of taping the stent to the graft, stent design, graft construction and/or any other consideration due to the construction of the stent graft, not all apices may be positioned under an adjacent pleat or may differ in the undulation height 1312 that can be positioned behind an adjacent pleat. Thus, there may be sections of the stent graft that may not be compressible in accordance with the instant invention. Thus, in another embodiment, only a section of the stent graft may be compressed by positioning confined apices under an adjacent pleat. In another embodiment, only a portion of the stent graft may be folded by positioning confined apices under an adjacent pleat (in the inner meridian), as depicted in FIG. 11. Although the disclosed embodiment comprises the apices in the first direction positioned behind pleats, the invention also encompasses apices in the second direction that are attached to the graft and are positioned under an adjacent pleat, while the apices in the first direction are not confined.

An important aspect of the invention is that the tape member, which comprises a first and second longitudinal edge, secures the stent member to the graft member and covers only a portion of the stent member. Specifically, said tape member is attached to said stent and to said graft such that the first edge of said tape member substantially covers of the apices in the first direction of the each of the undulations, thus confining the apices in the first direction of the undulations to the graft. In one embodiment, the first edge of said tape member is aligned to the edge of the apices in the first direction 814 of the each of the undulations, as essentially depicted in FIG. 14. With this construction when the stent graft is compressed, the graft forms circumferentially unidirectional pleats and allows said apices in the first direction 814 to be positioned under an adjacent pleat, as shown in FIGS. 9 and 11. The formation of said unidirectional pleats makes said stent graft more conformable, thus giving the stent graft the ability to bend, as depicted in FIG. 11. In one embodiment, said stent graft can bend to at least 90° without kinking (i.e. maintains an essentially circular cross-section in the luminal surface). In another embodiment, said stent graft can bend to at least 90° without kinking after in-vivo deployment.

The tape member has a generally broad and/or flat surface for interfacing with the stent and graft. This increases potential bonding surface area between the tape member and the graft member to enhance the structural integrity of the stent graft. The increased bonding surface area also facilitates minimizing the thickness of the tape member. In addition, the tape member is arranged in a helical configuration according to the embodiment illustrated in FIG. 14 (helically arranged tape member 1406). As shown, the tape member may be constructed with a constant width and arranged with uniform spacing between turns. Tape member 1406 not only covers the apices in the first direction of each of the undulations, but also covers a portion of each undulation. In another embodiment, there can be several tape members on a stent graft, which serves the same function as described above. A non-limiting reason to have several tape members on a stent graft is if there is a disruption in the stent pattern, such as changing the stent pattern to make room for a portal for a side-branch device, as depicted in FIG. 12, 1206, FIG. 14, 1408, and FIG. 1B, 121. In another embodiment, said tape member does not overlap an adjacent row of undulating stent members when the stent graft is not compressed. Although the Examples and Figures show an embodiment wherein apices in the first direction of the each of the undulations are attached to the stent graft by the tape member, said apices in the second direction may also be attached to the stent graft while the apices in the first direction are not attached.

Figure 13:
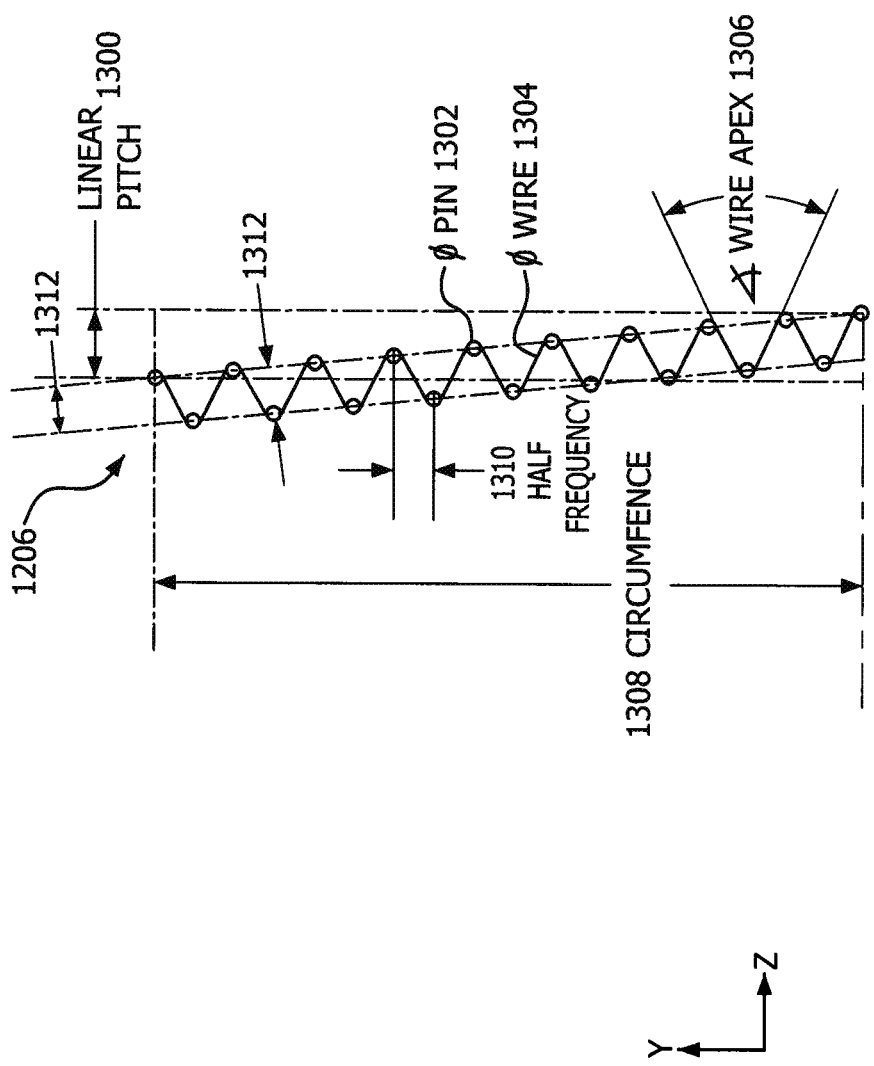
FIG. 13 depicts a single circumference winding pattern.

It has been found that the width of the tape member can affect the flexibility of the stent graft. The wider the tape member, the less flexible the stent graft will become. Thus, in one embodiment said tape member covers about 10%, about 20% about 30%, about 40%, about 50%, about 60%, about 70%, about 80% of undulation height 1312 (FIG. 13). In another embodiment, the full width of said tape member is adhered to said stent and graft. In another embodiment, said tape member does not extend to or touch an adjacent row of the undulating stent members, e.g. when not compressed or partially compressed. In another embodiment, the width of said unidirectional pleats is the same as the width of the tape member. Although the tape member can cover a portion of each undulation, including confining the apices in the first direction to the graft, as discussed above, apices in the second direction of the undulation are not confined relative to the graft (e.g. 816 in FIG. 8). This construction allows for the formation of pleats where the stent graft is compressed. Pleats can be fully circumferential when the stent graft is compress longitudinally, as depicted in FIG. 9, or in the inner meridian of a bend, as depicted in FIG. 11. In another embodiment, said unidirectional circumferential pleats are formed when initially compressed. In other words, no further manipulation of the stent graft is required to create said unidirectional circumferential pleats. In another embodiment, said unidirectional circumferential pleat are formed in-vivo when deployed. In another embodiment said pleats will be formed in the inner meridian in-vivo when said stent graft is deployed. Said stent graft of the invention can conform, as describe above, to the aortic arch or other tortuous, curved or bent body lumen. In another embodiment, tape member (or separate pieces thereof) also surrounds the terminal end portions of the stent graft to secure the terminal portions of the graft member to the support structure formed by stent member.

In another embodiment of the invention, the tape member is made from expanded PTFE (ePTFE) coated with an adhesive. In another embodiment, said adhesive is a thermoplastic adhesive. In another embodiment, said thermoplastic adhesive is fluorinated ethylene propylene (FEP). In this embodiment, the FEP-coated side faces toward and contacts the exterior surface of the stent and graft, thus attaching the stent to the graft. Although a particular tape member configuration and pattern has been illustrated and described, other configuration and/or patterns may be used without departing from the scope of the present invention.

In another embodiment of the invention, said stent graft of the invention comprises one or more radiopaque metallic fibers, such as gold, platinum, platinum-tungsten, palladium, platinum-iridium, rhodium, tantalum, or alloys or composites of these metals that may be incorporated into the device, particularly, into the graft, to allow fluoroscopic visualization of the device.

In another embodiment of the invention, said stent graft of the invention comprises optional sealing cuffs 808 and 812 as shown in FIG. 8. Said sealing cuff comprises a cuff which has a first cuff end secured to outer surface of the stent graft 800 and a second cuff end at least a portion of which is unsecured to form a flange. In this configuration, the flange forms a one-way valve that circumferentially surrounds the stent graft 800 and occludes flow around the stent graft. In one embodiment, said sealing cuff is positioned around the first end portion 806 of the stent graft 800. In another embodiment, said sealing cuff is positioned around the second end portion 810 of the stent graft 800. In another embodiment, said sealing cuff is positioned around the first end portion 806 and the second end portion 810 of the stent graft 800. In another embodiment, sealing cuffs (808, 812) comprise a hydrophilic material, preferably a hydrophilic polymer or gel-foam, which expands when exposed to water, such as in blood or other water-containing body fluids. In another embodiment, said sealing cuffs 808 and 812 can comprise the materials described above. A description of sealing cuffs is found in U.S. Pat. No. 6,015,431, incorporated by reference herein in its entirety for all purposes.

This invention is further illustrated by the following Examples which should not be construed as limiting. The contents of all Figures and references are incorporated herein by reference.

While particular embodiments of the present invention have been illustrated and described herein, the present invention should not be limited to such illustrations and descriptions. It should be apparent that changes and modifications may be incorporated and embodied as part of the present invention within the scope of the following claims.

EXAMPLE 1

Construction of a Highly Conformable Stent Graft

A flexible stent graft was assembled having the general configuration as shown in FIG. 8.

The stent graft was fabricated by initially extruding and expanding a tube of polytetrafluoroethylene (PTFE) to form a base tube. The base tube had a length of about 60 mm, a wall thickness of about 0.06 mm and a diameter of about 26 mm. The base tube had a substantial fibril orientation in the longitudinal direction so that the tube was relatively strong in the longitudinal direction while being relatively weak in the radial direction. The base tube was radially stretched over a mandrel having a diameter of about 31 mm.

To provide resistance to fluid permeation and to enhance the radial strength of the base tube, a film of densified ePTFE was wrapped over the base tube. The film was a thin, strong fluoropolymer; a particularly preferred material for this application is a non-porous ePTFE provided with an adhesive coating of thermoplastic fluorinated ethylene propylene (FEP), referred to hereinafter as "substantially impermeable ePTFE/FEP insulating tape". The FEP was oriented down against the base tube. EPTFE is well known in the medical device arts; it is generally made as described by U.S. Pat. Nos. 3,953,566 and 4,187,390 to Gore. The particular tape described herein is slit from a substantially non-porous ePTFE/FEP film having a thickness of about 0.0064 mm, an isopropyl bubble point of greater than about 0.6 MPa, a Gurley No. (permeability) of greater than 60 (minute/1 square inch/100 cc); (or 60 (minute/6.45 square cm/100 cc)), a density of 2.15 g/cc and a tensile strength of about 309 MPa in the length direction (i.e., the strongest direction). The film had a width of about 19 mm (0.75") with four passes helically wrapped with a pitch angle of about 86°.

To further enhance the radial strength of the base tube and to provide an open structure bonding layer, an additional layer of film was applied. The ePTFE film had high degree strength in the longitudinal direction and had a very open microstructure. The open microstructure enhanced the subsequent FEP/ePTFE bonding of a stent frame to the graft. The film had a thickness of about 2.5 microns (0.0001") and a width of about 25.4 mm (1.0"). Eight helically wrapped layers were applied with a pitch angle of about 83°.

The mandrel and wrapped films were then heat treated in an air convection oven to bond the films together.

Figure 12:
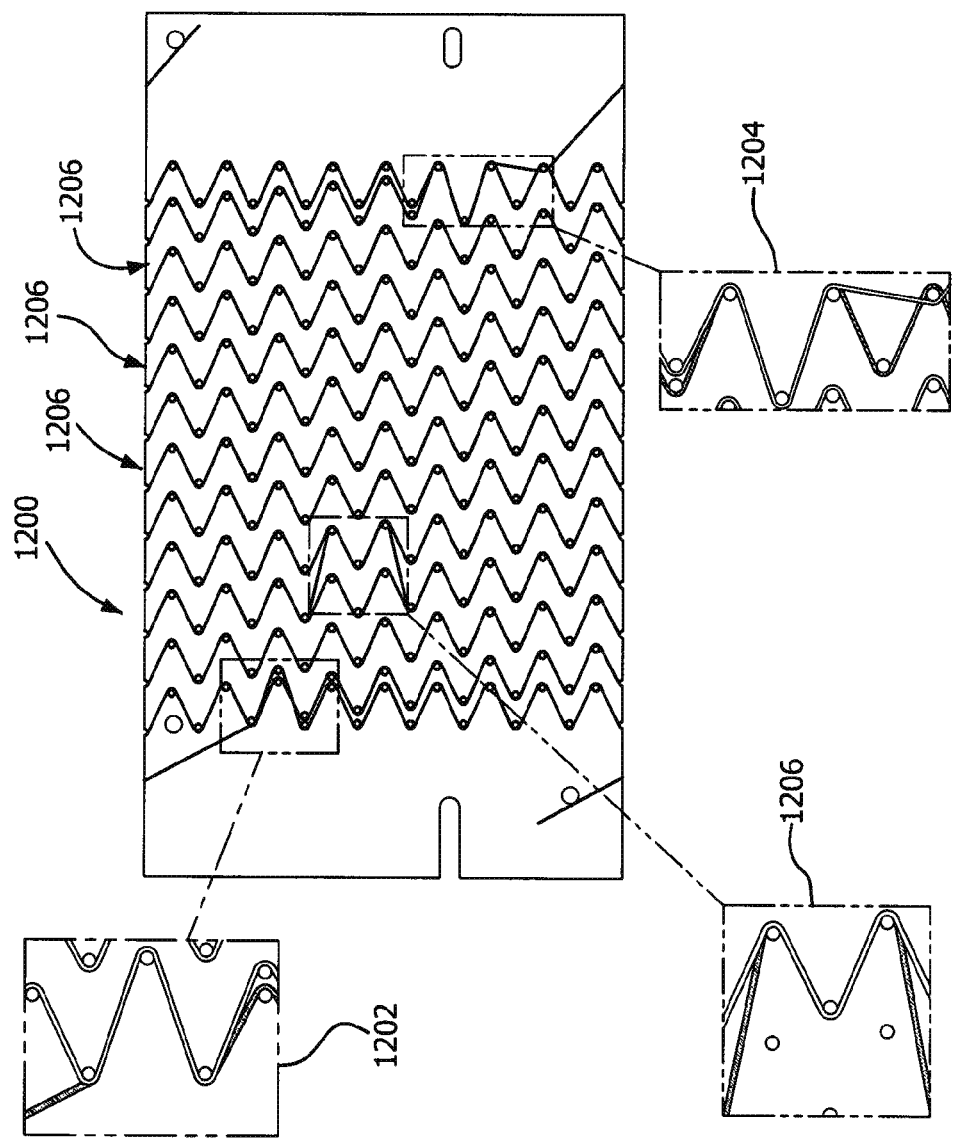
FIG. 12 depicts a "flat or unrolled" drawing of the cylindrical mandrel.

A stent frame was then formed by winding a Nitinol wire onto a mandrel having protruding pins. A "flat or unrolled" drawing of the cylindrical mandrel is shown in FIG. 12. Shown is an overall winding pattern 1200, detailing a first end portion 1202 and a second end portion 1204. Also shown is an optional "side branch portal" configuration 1206 that can be incorporated into the overall pattern if a branch portal is desired. The generic single circumference winding pattern shown as 1206 can replace the optional side branch pattern 1206 if desired.

Shown in FIG. 13 is a single circumference winding pattern shown as 1206. The pattern includes a linear pitch 1300, a pin diameter 1302, a wire diameter 1304, a wire apex angle 1306, a circumference 1308 and an apex to base half frequency 1310. The pattern shown was repeated along the stent length with the exception of the first and second end portions previously shown in FIG. 12 (1202, 1204). The optional side branch portal configuration (FIG. 12, 1206) was not incorporated.

The stent frame was formed according to the following dimensions as defined in FIG. 13: the linear pitch 1300 was about 9.7 mm (0.383"), the pin diameter 1302 was about 1.6 mm (0.063"), the wire diameter 1304 was about 0.5 mm (0.0195"), the wire apex angle 1306 was about 50.4 degrees, the circumference 1308 was about 97.3 mm (3.83") and the apex to base half frequency 1310 was about 5.3 mm (0.21").

The mandrel with the wound wire was then heat treated in an air convection oven as is commonly known in the art (e.g. see U.S. Pat. No. 6,352,561 to Leopold), and then quenched in room temperature water.

Figure 14:
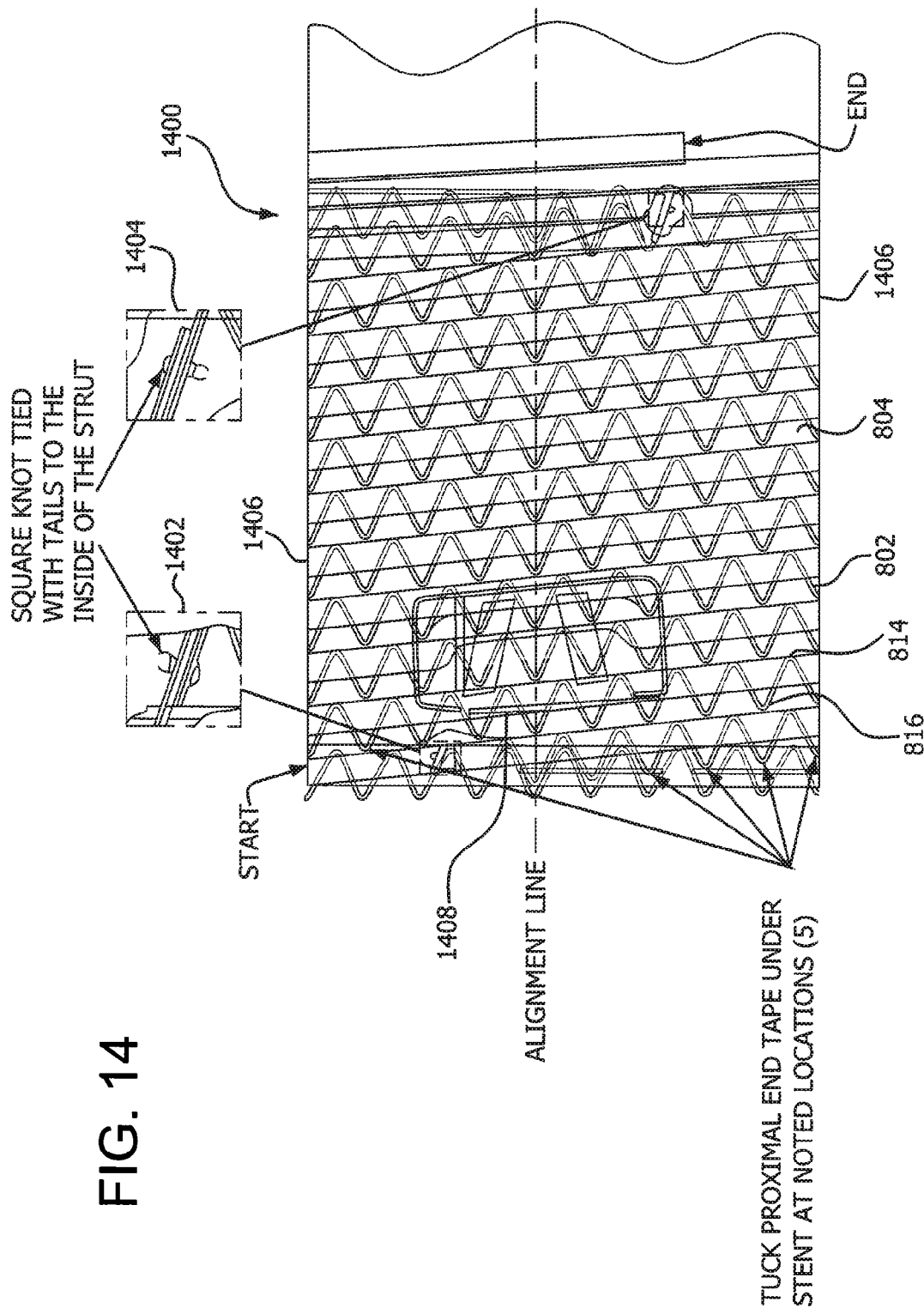
FIG. 14 depicts a stent graft having an undulating, helical wire stent surrounding a graft material. The stent is attached to the graft material by a helical a tape member.

The wire stent was the removed from the winding mandrel. The wire ends (shown in FIGS. 12, 1202 and 1204) were trimmed and tied together with high temperature fibers as shown in FIGS. 14, 1402 and 1404. The amplitude of the nested pair is longer than the adjacent apexes so that when the wires are nested the nested wires to not create an adversely high strained region (see FIGS. 14, 1410 and 1412). The stent was partially joined to the wrapped tube by melting the underlying FEP adjacent to portions of the stent wire using a soldering iron. A final layer of an ePTFE tape, laminated with FEP, was wrapped over the wire stent according to the pattern depicted in FIG. 14 and placed in an oven to bond the film to the underlying graft, thus securing the stent to the graft.

Shown in FIG. 14 is a stent graft 1400 having an undulating, helical wire stent 802 surrounding a graft material 804. The stent is attached to the graft material by a helically applied tape member 1406. As shown, the first edge of the helically applied tape member 1406 covers the opposing first apices 814 of the wire stent. An optional wrapping pattern section 1408 can be incorporated if a side branch portal is desired. The tape 1406 was an ePTFE/FEP laminate having a width of about 5.5 mm (0.215") and a thickness of about 10 microns (0.0004"). The tape was partially joined to the wrapped tube by melting the underlying FEP adjacent to portions of the stent wire using a soldering iron. A sacrificial compression tape was helically wrapped onto the stent graft. The compression tape was about 51 mm (2") wide, about 0.5 mm (0.02") thick and was wrapped with an approximate 50% overlap. An additional sacrificial film was wrapped to assist in the subsequent heat treatment compression step. This film was an ePTFE tape having a longitudinal fibril/strength orientation, a thickness of about 2.5 microns (0.0001") and a width of about 51 mm (2"). Five passes were applied with an approximate 50% overlap between the film layers.

The assembly was then heat treated in an air convection oven to bond the film layers together (as essentially described in U.S. Pat. No. 6,352,561 to Leopold). During this heat treat cycle, the film compressed down against the mandrel causing the melted FEP to flow into the underlying film layers, joining the graft layers together along with the wire stent. After cooling the sacrificial film compression layers were removed, the ends of the graft material were trimmed to length and the stent graft was removed from the mandrel. The resulting stent graft is depicted in FIG. 8, with the exception of the optional sealing cuffs (FIG. 8, 806, 810).

EXAMPLE 2

Construction of a Highly Conformable Stent Graft Having an Integral Side Branch Portal Referring to FIGS. 2A and 2B, a metallic mandrel 200 was fabricated having a slot 202 formed into one end of the mandrel. The slot 202 terminates onto a back wall 204. The mandrel had a diameter of about 31 mm and the slot was about 12.5 mm wide, by about 10 mm deep and about 13 cm long. As shown in FIG. 2B, an inner tube 206 was radially stretched onto the mandrel 200, covering a portion of the mandrel groove 202. The inner tube was an extruded and expanded tube of polytetrafluoroethylene (PTFE). The inner tube had a length of about 60 mm, a wall thickness of about 0.06 mm and a diameter of about 26 mm. The inner tube had a substantial fibril orientation in the longitudinal direction so that the tube was relatively strong in the longitudinal direction while being relatively weak in the radial direction.

As shown in FIG. 3A the mandrel 200 was covered by the inner tube 206. The inner tube was cut, forming a slit 300 at the back wall 204 of the mandrel groove 202.

To further strengthen the inner tube (FIG. 3A, 206), two additional polymeric sheets were added onto the inner tube prior to the insertion of the secondary stent assembly. The strengthening layers were then deformed into the mandrel groove, providing additional support to the inner tube/secondary stent assembly. The strengthening layers comprised densified ePTFE provided with an adhesive coating of thermoplastic fluorinated ethylene propylene (FEP) referred to hereinafter as "substantially impermeable ePTFE/FEP insulating tape". The FEP of the strengthening layers was oriented towards the base tube. EPTFE is well known in the medical device arts; it is generally made as described by U.S. Pat. Nos. 3,953,566 and 4,187,390 to Gore. The particular strengthening layers described herein were slit from a substantially non-porous ePTFE/FEP film having a thickness of about 0.0064 mm, an isopropyl bubble point of greater than about 0.6 MPa, a Gurley No. (permeability) of greater than 60 (minute/1 square inch/100 cc); (or 60 (minute/6.45 square cm/100 cc)), a density of 2.15 g/cc and a tensile strength of about 309 MPa in the length direction (i.e., the strongest direction). The first strengthening layer was about 25 mm wide by about 25 mm long and was centered over the mandrel slot about 15 mm from the slot back wall (towards the end of the mandrel). The second strengthening layer was about 25 mm wide and about 40 mm long and was centered over the mandrel slot abutting the slot back wall 204.

As shown in FIG. 3B, a secondary stent assembly 302 was aligned to the mandrel groove 202, mandrel back wall 204, strengthening layers and inner tube slit 300. A first support segment (subsequently described) was placed into the secondary stent assembly and the secondary stent assembly 302 (with the first support segment) was then inserted into the mandrel groove 202, deforming the inner tube 206 (and strengthening layers) into the mandrel groove. The back wall 204 defined the opening in the innermost tube (130, FIG. 1E).

To control the deformed shape of the inner tube, a support segment was placed into the secondary stent assembly and into the mandrel groove, as depicted in FIGS. 4A and 4B. Shown in FIG. 4A is a side view schematic of the mandrel 200, the groove 202 and the groove back wall 204. Shown in FIG. 4B is a side view schematic of the mandrel 200, mandrel groove 202 and inner tube 206. The secondary stent assembly 302 was placed over a first support segment 400 having an end formed to mate to the mandrel groove back wall 204. The opposing end of the first support segment had a tapered or angulated wall as depicted in FIG. 4B. A second support segment 402 was placed into the mandrel groove 202 under the inner tube 206. The second support structure had flat walls and was used to hold of the first support structure 400 in place. The inner tube 206 is shown deformed into the mandrel groove 202. The inner tube 206 is also shown having a tapered, beveled or angulated wall portion 404 formed by the angulated wall of support segment 400.

A secondary stent assembly was assembled as outlined in FIGS. 5A through 5D. As shown in FIGS. 5A and 5B, a polymeric tube 502 was slip-fit onto a mandrel 500. The tube was formed from a film of the same material used for the strengthening layers as previously described. The film was helically wrapped onto a mandrel having a diameter of about 8 mm with the FEP layer oriented away from the mandrel. The wrapped mandrel was then heat set to fuse the FEP/ePTFE layers forming a tube. An undulating wire was formed into a ring stent 506 by winding the wire onto a mandrel with protruding pins. The diameters of the mandrel and pins along with the locations of the pins dictated the final configuration of the ring stent. The wire was Nitinol and had a diameter of about 0.15 mm. The undulating stent pattern had an apex to apex length of about 5 mm. After the wire was wound onto the mandrel, the mandrel and wire were heat treated and quenched in room temperature water to set the shape of the stent. The wire was then removed from the mandrel. The ends of the wire were joined together with a section of polymeric heat shrink tubing, forming ring stent 506. Two of these ring stents 506 were then placed onto the polymeric tube 502. Radiopaque gold marker bands 504 were then placed onto the polymeric tube 502.

Next, as shown in FIG. 5C, one end of the polymeric tube 502 was inverted and drawn over the wire ring stents 506 and radiopaque marker bands 504. The mandrel, polymeric tube, ring stents and radiopaque bands were then heat treated to bond the components together into a stent assembly. The assembly was removed from the mandrel and trimmed to length, forming a secondary stent assembly 302 as shown in FIG. 5D. The secondary stent assembly was then placed onto a first support segment 400.

As previously described (FIG. 4B), the secondary stent (or secondary stent assembly) and the first support assembly were then inserted into the mandrel groove 202, deforming the inner tube 206 into the mandrel groove. A second support segment 402 was placed into the mandrel groove 202 under the inner tube 206. The assembly shown in FIG. 4B was then covered with an outer support film. The support was formed from a film of the same material used for the strengthening layers as previously described. The film was about 30 mm wide by about 27 mm wide and was centered over the mandrel slot about 6 mm behind the slot back wall (away from the mandrel end). The FEP layer was oriented down toward the mandrel.

To provide resistance to fluid permeation and to enhance the radial strength of the base tube, a film of densified ePTFE was wrapped over the base tube. The film was a thin, strong fluoropolymer; a particularly preferred material for this application is a non-porous ePTFE provided with an adhesive coating of thermoplastic fluorinated ethylene propylene (FEP), referred to hereinafter as "substantially impermeable ePTFE/FEP insulating tape". The FEP was oriented down against the base tube. EPTFE is well known in the medical device arts; it is generally made as described by U.S. Pat. Nos. 3,953,566 and 4,187,390 to Gore. The particular tape described herein is slit from a substantially non-porous ePTFE/FEP film having a thickness of about 0.0064 mm, an isopropyl bubble point of greater than about 0.6 MPa, a Gurley No. (permeability) of greater than 60 (minute/1 square inch/100 cc); (or 60 (minute/6.45 square cm/100 cc)), a density of 2.15 g/cc and a tensile strength of about 309 MPa in the length direction (i.e., the strongest direction). The film had a width of about 19 mm (0.75") with four passes helically wrapped with a pitch angle of about 86°.

To further enhance the radial strength of the base tube and to provide an open structure bonding layer, an additional layer of film was applied. The ePTFE film had a high degree strength in the longitudinal direction and had a very open microstructure. The open microstructure enhanced the subsequent FEP/ePTFE bonding of a stent frame to the graft. The film had a thickness of about 2.5 microns (0.0001") and a width of about 25.4 mm (1.0"). Eight helically wrapped layers were applied with a pitch angle of about 83°.

The mandrel and wrapped films were then heat treated in an air convection oven to bond the film layers together.

A stent frame was then formed by winding a Nitinol wire onto a mandrel having protruding pins. A "flat or unrolled" drawing of the cylindrical mandrel is shown in FIG. 12. Shown is an overall winding pattern 1200, detailing a first end portion 1202 and a second end portion 1204. Also shown is a "side branch portal" configuration 1206 that was incorporated into the overall pattern to form a branch portal.

Shown in FIG. 13 is a single circumference winding pattern shown as 1206. The pattern includes a linear pitch 1300, a pin diameter 1302, a wire diameter 1304, a wire apex angle 1306, a circumference 1308 and an apex to base half frequency 1310. The pattern shown was repeated along the stent length with the exception of the first and second end portions previously shown in FIG. 12 (1202, 1204). The optional side branch portal configuration (FIG. 12, 1206) was incorporated.

The stent frame was formed according to the following dimensions as defined in FIG. 13: the linear pitch 1300 was about 9.7 mm (0.383"), the pin diameter 1302 was about 1.6 mm (0.063"), the wire diameter 1304 was about 0.5 mm (0.0195"), the wire apex angle 1306 was about 50.4 degrees, the circumference 1308 was about 97.3 mm (3.83") and the apex to base half frequency 1310 was about 5.3 mm (0.21").

The mandrel with the wound wire was then heat treated in an air convection oven as is commonly known in the art and then quenched in room temperature water.

The wire stent was the removed from the winding mandrel. The wire ends (shown in FIGS. 12, 1202 and 1204) were trimmed and tied together with high temperature fibers as shown in FIGS. 14, 1402 and 1404. The wire stent was then placed onto the previously film wrapped tube/mandrel. The stent was partially joined to the wrapped tube by melting the underlying FEP adjacent to portions of the stent wire using a soldering iron. A final layer of an ePTFE tape, laminated with FEP was wrapped over the wire stent according to the pattern depicted in FIG. 14.

Shown in FIG. 14 is a stent graft 1400 having an undulating, helical wire stent 802 surrounding a graft material 804. The stent was attached to the graft material by a helically applied tape member 1406. As shown, the first edge of the helically applied tape member 1406 covers the opposing first apices 814 of the wire stent. The wrapping pattern section 1408 was incorporated to form a side branch portal. The tape 1406 was an ePTFE/FEP laminate having a width of about 5.5 mm (0.215") and a thickness of about 10 microns (0.0004"). The tape was partially joined to the wrapped tube by melting the underlying FEP adjacent to portions of the stent wire using a soldering iron. A sacrificial compression tape was helically wrapped onto the stent graft. The compression tape was about 51 mm (2") wide, about 0.5 mm (0.02") thick and was wrapped with an approximate 50% overlap. An additional sacrificial film was wrapped to assist in the subsequent heat treatment compression step. This film was an ePTFE tape having a longitudinal fibril/strength orientation, a thickness of about 2.5 microns (0.0001") and a width of about 51 mm (2"). Five passes were applied with an approximate 50% overlap between the film layers.

The assembly was then heat treated in an air convection oven to bond the film layers together. During this heat treat cycle, the film compressed down against the mandrel causing the melted FEP to flow into the underlying film layers, joining the graft layers together along with the wire stent. After cooling the sacrificial film compression layers were removed, the ends of the graft material were trimmed to length and the stent graft was removed from the mandrel. The resulting stent graft is depicted in FIG. 8, with the exception of the optional sealing cuffs (FIG. 8, 806, 810).

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A method of making a multi-lumen stent graft comprising:
    covering a first mandrel that comprises a groove and a back wall of said groove with an innermost polymeric tube;
    slitting said innermost polymeric tube along said back wall of said groove;
    placing a second mandrel into said groove of the first mandrel and aligning said second mandrel with the back wall of the groove, deforming said innermost polymeric tube;
    placing an outermost polymeric tube over said innermost polymeric tube; and
    cutting an opening in said outermost polymeric tube over said second mandrel;
    wherein said outermost polymeric tube and innermost polymeric tube comprise a graft member.

2. The method of claim 1, wherein a primary stent is placed over said graft member.

3. The method of claim 2, wherein said primary stent is attached to said graft member by coupling member.

4. The method of claim 2, wherein said primary stent comprises undulations.

5. The method of claim 4, wherein said undulations are in-phase.

6. The method of claim 1, wherein said outermost polymeric tube comprises ePTFE.

7. The method of claim 1, wherein said innermost polymeric tube comprises ePTFE.

8. The method of claim 1, wherein there is a secondary stent or stent assembly around said second mandrel.

9. The method of claim 8, wherein said secondary stent or stent assembly abuts at least a portion of the innermost tube.

10. The method of claim 1, wherein the slitting of the innermost polymeric tube and making of an opening in the outermost polymeric tube creates a secondary lumen that is in fluid communication through said openings.

* * * * *